(12) United States Patent
Morikawa et al.

(10) Patent No.: US 9,078,725 B2
(45) Date of Patent: Jul. 14, 2015

(54) ELECTROENCEPHALOGRAM INTERFACE SYSTEM, ELECTROENCEPHALOGRAM INTERFACE PROVIDING APPARATUS, METHOD OF OPERATING ELECTROENCEPHALOGRAM INTERFACE, AND PROGRAM

(75) Inventors: Koji Morikawa, Kyoto (JP); Yoshihisa Terada, Tokyo (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 897 days.

(21) Appl. No.: 13/305,916

(22) Filed: Nov. 29, 2011

(65) Prior Publication Data

US 2012/0069247 A1    Mar. 22, 2012

Related U.S. Application Data

(63) Continuation of application No. PCT/JP2011/000215, filed on Jan. 18, 2011.

(30) Foreign Application Priority Data

Feb. 25, 2010    (JP) .................................. 2010-040337

(51) Int. Cl.
*G06N 5/04*    (2006.01)
*A61F 4/00*    (2006.01)
(Continued)

(52) U.S. Cl.
CPC . *A61F 4/00* (2013.01); *G06F 3/015* (2013.01); *A61B 5/04842* (2013.01); *A61B 2218/00* (2013.01); *G06N 5/04* (2013.01)

(58) Field of Classification Search
None
See application file for complete search history.

(56) References Cited

U.S. PATENT DOCUMENTS

2006/0114222 A1    6/2006    Araki et al.
2009/0187114 A1    7/2009    Morikawa et al.
(Continued)

FOREIGN PATENT DOCUMENTS

CN    101506757 A    8/2009
JP    2004-275619 A    10/2004
(Continued)

OTHER PUBLICATIONS

Forbin, et al., Flicker Compensation for Archived Film Sequences Using a Segmentation-Based Nonlinear Model, EURASIP Journal on Advances in Signal Processing, 2008, pp. 1-16.*

(Continued)

*Primary Examiner* — Wilbert L. Starks
(74) *Attorney, Agent, or Firm* — Renner, Otto, Boisselle & Sklar, LLP

(57) ABSTRACT

An electroencephalogram interface system includes: a presentation section for presenting multiple options to a user, the multiple options being manipulable items concerning manipulations of a device; a selection flicker control section for flickering each option; an inference section for inferring one option corresponding to a desired manipulation of the user by utilizing an event-related potential of an electroencephalogram of the user, the event-related potential being based on the flickering of each option as a starting point; a confirmation flicker control section for effecting confirmation flickering of the one option inferred; a determination section for determining whether the inferred option corresponds to the desired manipulation of the user by utilizing an event-related potential of the user's electroencephalogram, the event-related potential being based on the confirmation flickering of the one option as a starting point; and an output section for executing a process which is in accordance with the determined result.

17 Claims, 14 Drawing Sheets

(51) Int. Cl.
*G06F 3/01* (2006.01)
*A61B 5/0484* (2006.01)

(56) References Cited

U.S. PATENT DOCUMENTS

| | | | |
|---|---|---|---|
| 2010/0004556 A1 | 1/2010 | Adachi et al. | |
| 2010/0106042 A1 | 4/2010 | Morikawa et al. | |
| 2010/0317988 A1 | 12/2010 | Terada et al. | |

FOREIGN PATENT DOCUMENTS

| | | |
|---|---|---|
| JP | 2005-034620 A | 2/2005 |
| JP | 2010-015584 A | 1/2010 |
| WO | 2009/057278 A1 | 5/2009 |
| WO | WO 2009/057260 A1 | 5/2009 |

OTHER PUBLICATIONS

Form PCT/ISA/237 for corresponding International Application No. PCT/JP2011/000215 dated Apr. 26, 2011 and Partial English translation.

International Search Report for corresponding International Application No. PCT/JP2011/000215 mailed Apr. 26, 2011.

Donchin et al., "The Mental Prosthesis: Assessing the Speed of a P300-Based Brain-Computer Interface", IEEE Transactions on Rehabilitation Engineering, vol. 8, No. 2, Jun. 2000.

Hiroshi Nittono, "Event-Related Potential Guidebook for Psychology", Kitaoji Shobo, 2005, p. 69.

Chinese Search Report dated Sep. 17, 2014 for corresponding Chinese Application No. 201180002726.3 and English translation.

\* cited by examiner

FIG.4
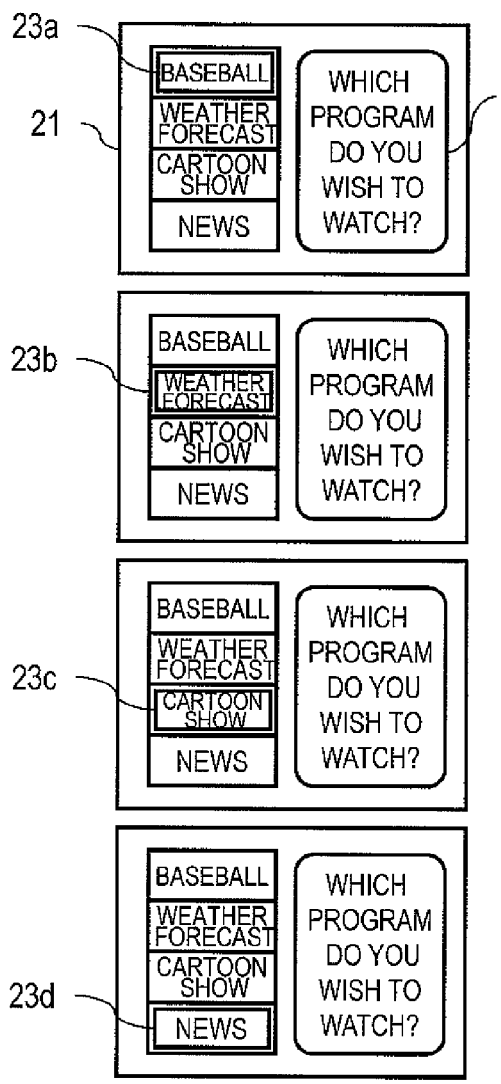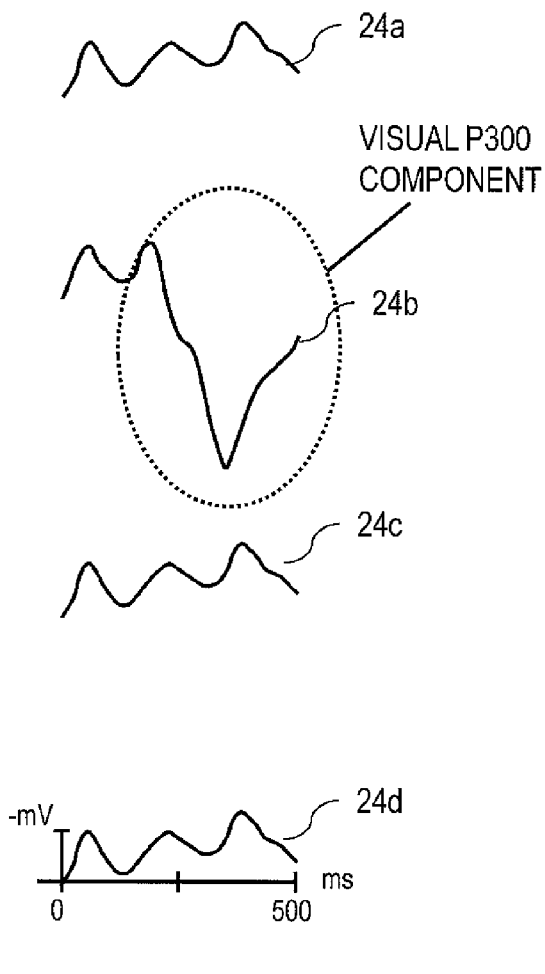
(a)          (b)

FIG. 7

| | NUMBER OF FLICKERS FOR EACH OPTION | NUMBER OF CONFIRMATION FLICKERS | TOTAL NUMBER OF FLICKERS SELECTION/ DETERMINATION TIME | INTENTION-EXPRESSING TIME (FIRST TIME AVERAGE) | DISTINCTION ACCURACY (INCLUDING ASSUMPTION) |
|---|---|---|---|---|---|
| | 41 | 42 | 43 | 44 | 45 |
| CONVENTIONAL METHOD A (HITHERTO-USED METHOD) | 5 | - | 20 TIMES 7 SECONDS | 7 SECONDS | 66.7% |
| CONVENTIONAL METHOD B (NUMBER OF SUMMATIONS IS SIMPLY INCREASED) | 10 | - | 40 TIMES 14 SECONDS | 14 SECONDS | 77.5% |
| SELECTION + CONFIRMATION | 5 | 10 | 30 TIMES 7+3.5 SECONDS | 7 SECONDS+ 1.2 SECONDS | 78.8% |

| ORDINAL RANK OF AMPLITUDE OF CORRECT OPTION | NUMBER OF TRIALS |
|---|---|
| 1ST (CORRECT) | 69 |
| 2ND | 14 |
| 3RD | 7 |
| 4TH | 6 |
| TOTAL | 96 |

NOT CORRECTED: 1ST RANK ONLY =72%
CORRECTED: 1ST RANK + 2ND RANK =87%

(Donchin 2000)

ELECTROENCEPHALOGRAM INTERFACE SYSTEM, ELECTROENCEPHALOGRAM INTERFACE PROVIDING APPARATUS, METHOD OF OPERATING ELECTROENCEPHALOGRAM INTERFACE, AND PROGRAM

This is a continuation of International Application No. PCT/JP2011/000215, with an international filing date of Jan. 18, 2011, which claims priority of Japanese Patent Application No. 2010-040337, filed on Feb. 25, 2010, the contents of which are hereby incorporated by reference.

BACKGROUND OF THE INVENTION

1. Field of the Invention

The present invention relates to an electroencephalogram interface system for inferring an intent of a user by utilizing an electroencephalogram. More specifically, the present invention relates to an electroencephalogram interface system having a function of confirming whether an inferred intent of a user (a selected option) is correct or not.

2. Description of the Related Art

Devices having various functions for use in daily life have been proposed. By using such devices, users may obtain desired information or enjoy the services provided by the devices.

In recent years, due to an increase in the number of devices themselves and an increase in the information that cannot be obtained without using devices, there have been increasing needs for facilitating a user's manipulation of an interface for allowing the user to give instructions for device manipulations. In information devices (television sets, mobile phones, PDAs, etc.), for example, a user makes device manipulations as he or she selects an option which is a manipulable item (menu item) on of the information device, while looking at the screen. As method for making such manipulation inputs, methods such as pressing a button, moving a cursor and making a confirmation, or manipulating a mouse while watching a screen have been used. However, it may have been impossible to execute a manipulation when both hands are unavailable, due to tasks other than device manipulations, e.g., household chores, rearing of children, and driving an automobile.

In answer thereto, there are input methods utilizing biological signals from a user. Donchin et al., "The Mental Prosthesis: Assessing the Speed of a P300-Based Brain-Computer Interface", IEEE TRANSACTIONS ON REHABILITATION ENGINEERING, Vol. 8, No. 2, June 2000 discloses a technique that utilizes an event-related potential of an electroencephalogram for distinguishing an option which a user wishes to select. Specifically, options are randomly highlighted, and the waveform of an event-related potential (often referred to as a P300 component) which appears about 300 milliseconds after a point in time that an option that the user wishes to select was highlighted is utilized to enable an inference of an option.

As used herein, an "event-related potential" refers to a transient potential fluctuation in the brain, which is a portion of the electroencephalogram and which occurs in temporal relationship with an external or internal event.

According to this technique, even in a situation where both hands are full, or even in a situation where the user is unable to move his or her limbs due to an illness or the like, the user can select an option which they wish to select, whereby an interface for device manipulations, etc., can be realized. Also in Japanese Laid-Open Patent Publication No. 2004-275619 (an example of P300-BCI), an example of an electroencephalogram interface which similarly utilizes an event-related potential is described.

However, an electroencephalogram signal is a weak signal that has fluctuations, and contains a lot of noise. It is difficult to completely prevent mixing of noise. Oftentimes, a desired event-related potential cannot be obtained from a single electroencephalogram measurement, and it is not always the case that a user's intent can be accurately determined.

Therefore, a method is known which acquires an event-related potential over plural times under the same condition, and takes an arithmetic mean thereof, thus obtaining only a desired electroencephalogram component by counteracting noise components which occur unconditionally. In physiopsychological experimentation and the like, it is supposed that an event-related potential must be obtained through a summation over several dozens of times. For example, Hiroshi NITTONO, "Event-Related Potential Guidebook For Psychology", Kitaoji Shobo, 2005, p. 69 states that "supposedly, in the case of a large potential exceeding 10 $\mu$V, such as the P3 (P300) which is the target of this measurement, a summation over about 20 times is required to obtain a stable waveform".

FIG. 16 shows a relationship between the number of summations and the distinction ratio for an event-related potential in an electroencephalogram interface. FIG. 16 is FIG. 3 taken from Donchin et al., supra, being modified so that the horizontal axis reads as the number of summations.

In FIG. 16, the horizontal axis represents the number of summations, and the vertical axis represents the distinction ratio, in the electroencephalogram interface of Donchin et al., supra. The two lines shown in FIG. 16 represent results of different analysis methods. FIG. 16 would indicate that the distinction ratio improves as the number of summations is increased, and that a 100% distinction rate is not attained unless the number of summations is adequate. For example, although a near 100% distinction ratio is obtained from a summation over 16 times and 32 times, only a 30 to 50% distinction ratio is obtained from a summation over 1 or 2 times. It is reported in many distinction techniques that an about 80% to 90% distinction rate is achieved by using an arithmetic mean waveform over plural times. This situation means that, when an electroencephalogram interface is used, it is not guaranteed that the device can make a correct determination with respect to every manipulation. It means that one or two unsuccessful instances will be included among about ten manipulations.

Japanese Laid-Open Patent Publication No. 2005-34620 (a second example of P300-BCI, including also displaying of the number of summations) also discloses results of studying the number of summations for an event-related potential. In paragraph 0050 of Japanese Laid-Open Patent Publication No. 2005-34620, the number of summations is experimentally varied from 8 times to 22 times for each of five words. The experimental results in this case are shown in Table 2 at paragraph 0058 of Japanese Laid-Open Patent Publication No. 2005-34620. In this laid-open patent publication, it is reported that the number of summations that provides the highest distinction ratio is 10 to 20 times.

Basically, as the number of summations increases, noise influences are reduced and thus the distinction accuracy is expected to improve. However, as the number of summations increases, the amount of time that the user needs to pay attention to the interface increases. In Japanese Laid-Open Patent Publication No. 2005-34620, the options need to flicker as often as 100 times. While the options flicker 100 times, the test subject needs to wait for the very option of selection to be lit, and actually think that he or she wants to select it when it is lit. Thus, the test subject needs to maintain a conscious state of attention for a long time. The time required to make a selection depends on the flickering period. In this laid-open patent publication, it is supposed that 100 times of presentation take about one minute (paragraph 0050 of Japanese Laid-Open Patent Publication No. 2005-34620).

To summarize all of the above, it can be said that there is a trade off relationship between improving the distinction accuracy by increasing the number of summations and reducing the amount of time that the user pays attention to the interface by decreasing the number of summations.

SUMMARY OF THE INVENTION

An objective of the present invention is to, in the selection of an item in an electroencephalogram interface, reconcile improvement in the distinction accuracy and reduction in the intent-expressing time.

An electroencephalogram interface system according to the present invention includes: a presentation section for presenting a plurality of options to a user, the plurality of options being manipulable items concerning manipulations of a device; a selection flicker control section for flickering each of the plurality of options; a biological signal detection section for measuring an electroencephalogram signal from the user; an inference section for inferring one option corresponding to a desired manipulation of the user by utilizing an event-related potential of an electroencephalogram contained in the electroencephalogram signal, the event-related potential being based on the flickering of each of the plurality of options as a starting point; a confirmation flicker control section for effecting confirmation flickering of the one option inferred; a determination section for determining whether the inferred option corresponds to the desired manipulation of the user by utilizing an event-related potential of an electroencephalogram contained in the electroencephalogram signal, the event-related potential being based on the confirmation flickering of the one option as a starting point; and an output section for executing a process which is in accordance with a result of determination by the determination section.

At least one of the inference section and the confirmation flicker control section may adjust the number of times of flickering each of the plurality of options and/or the number of confirmation flickers, by using event-related potentials having been acquired up to a given point in time.

At least the confirmation flicker control section may adjust the number of confirmation flickers; and by using the event-related potentials having been acquired up to the given point in time, the confirmation flicker control section may calculate a certainty level, the certainty level being an index indicating how certain the option inferred by the inference section is to the user, and decrease the number of confirmation flickers if the certainty level is high, or increase the number of confirmation flickers if the certainty level is low.

At least the confirmation flicker control section may adjust the number of confirmation flickers; the determination section may calculate a certainty level concerning presence or absence of a request for changing the inferred option by using an event-related potential concerning the confirmation flickering; when the certainty level is equal to or greater than a predetermined threshold value, the determination section may categorize the certainty level to be high, and the confirmation flicker control section may decrease the number of confirmation flickers; and when the certainty level is smaller than the predetermined threshold value, the determination section may categorize the certainty level to be low, and the confirmation flicker control section may increase the number of confirmation flickers.

The determination section may calculate a certainty level concerning presence or absence of a request for changing the inferred option by using a similarity level, the similarity level being calculated based on a waveform of an event-related potential for the confirmation flickering and a prestored template waveform for use when a request of a retrial is made.

By utilizing a proportion with which a result or results of inference by the inference section are determined by the determination section as incorrect, the selection flicker control section may adjust the number of flickers for each option.

When a result of inference by the inference section is determined by the determination section as incorrect, the selection flicker control section may increase the number of flickers for each option if a proportion with which the result or results of inference are determined as incorrect is equal to or greater than a predetermined value, and the selection flicker control section may decrease the number of flickers for each option if the proportion with which the result or results of inference are determined as incorrect is smaller than the predetermined value.

The number of confirmation flickers controlled by the confirmation flicker control section may be larger than the number of selection flickers controlled by the selection flicker control section.

The inference section may infer an option for which a predetermined component of the event-related potential takes a largest amplitude to be the option corresponding to the desired manipulation of the user; and when the inferred option is determined by the determination section as incorrect, the inference section may re-infer an option for which the predetermined component takes a second largest amplitude to be the option corresponding to the desired manipulation of the user.

The inference section may infer the option corresponding to the desired manipulation of the user by using a positive local maximum of an event-related potential from 200 milliseconds to 400 milliseconds based on the flickering of each option as a starting point, or a negative local minimum of an event-related potential from 100 milliseconds to 300 milliseconds based on the flickering of each option as a starting point.

In determining whether the inferred option is the option corresponding to the desired manipulation of the user, the determination section may use P300 or N200, where P300 is a positive local maximum of an event-related potential from 200 milliseconds to 400 milliseconds based on the confirmation flickering of the inferred option as a starting point, and N200 is a negative local minimum of an event-related potential from 100 milliseconds to 300 milliseconds based on the confirmation flickering of the inferred option as a starting point.

The inference section may infer an option that corresponds to, among event-related potentials based on the flickering of the plurality of options as starting points, an event-related potential having a predetermined characteristic component to be the one option corresponding to the desired manipulation of the user.

When an event-related potential based on the flickering of the one option as a starting point contains a predetermined characteristic component, the determination section may determine that the one option corresponds to the desired manipulation of the user; and when an event-related potential based on the flickering of the one option as a starting point does not contain the predetermined characteristic component, the determination section may determine that the one option does not correspond to the desired manipulation of the user.

An electroencephalogram interface providing apparatus according to the present invention comprises: a selection flicker control section for flickering each of plurality of options on a presentation section, the plurality of options being manipulable items concerning manipulations of a device; an inference section for inferring one option corresponding to a desired manipulation of the user by utilizing an event-related potential of an electroencephalogram contained in an electroencephalogram signal from the user measured by a biological signal detection section, the event-related potential being based on the flickering of each of the plurality of options as a starting point; a confirmation flicker control section for effecting confirmation flickering of the one option inferred; and a determination section for determining whether the inferred option corresponds to the desired manipulation of the user by utilizing an event-related potential of an electroencephalogram contained in the electroencephalogram signal, the event-related potential being based on the confirmation flickering of the one option as a starting point, wherein the electroencephalogram interface providing apparatus causes an output section to execute a process which is in accordance with a result of determination by the determination section.

A method of operating an electroencephalogram interface system comprises the steps of: presenting a plurality of options to a user, the plurality of options being manipulable items concerning manipulations of a device; flickering each of the plurality of options; measuring an electroencephalogram signal from the user; inferring one option corresponding to a desired manipulation of the user by utilizing an event-related potential of an electroencephalogram contained in the electroencephalogram signal, the event-related potential being based on the flickering of each of the plurality of options as a starting point; effecting confirmation flickering of the one option inferred; determining whether the inferred option is an option corresponding to the desired manipulation of the user by utilizing an event-related potential of an electroencephalogram contained in the electroencephalogram signal, the event-related potential being based on the confirmation flickering of the one option as a starting point; and executing a process which is in accordance with a result of determination by the determination step.

A computer program according to the present invention is a computer program to be executed by a computer mounted in an electroencephalogram interface providing apparatus, wherein the computer program causes the computer to execute the steps of: causing a presentation section to present a plurality of options, the plurality of options being manipulable items concerning manipulations of a device; flickering each of the plurality of options; receiving an electroencephalogram signal from the user measured by a biological signal detection section; inferring one option corresponding to a desired manipulation of the user by utilizing an event-related potential of an electroencephalogram contained in the electroencephalogram signal, the event-related potential being based on the flickering of each of the plurality of options as a starting point; effecting confirmation flickering of the one option inferred; determining whether the inferred option is an option corresponding to the desired manipulation of the user by utilizing an event-related potential of an electroencephalogram contained in the electroencephalogram signal, the event-related potential being based on the confirmation flickering of the one option as a starting point; and causing an output section to execute a process which is in accordance with a result of determination by the determination step.

With an electroencephalogram interface system according to the present invention, when an apparatus has incorrectly determined a user's desired option, the incorrectness of the determination can be detected, based on which a retrial and/or an automatic error correction is realized. As a result, a user's intent can be efficiently expressed via an electroencephalogram interface, thus improving the efficiency of interface manipulation by the user.

Other features, elements, processes, steps, characteristics and advantages of the present invention will become more apparent from the following detailed description of preferred embodiments of the present invention with reference to the attached drawings.

Figure 3:
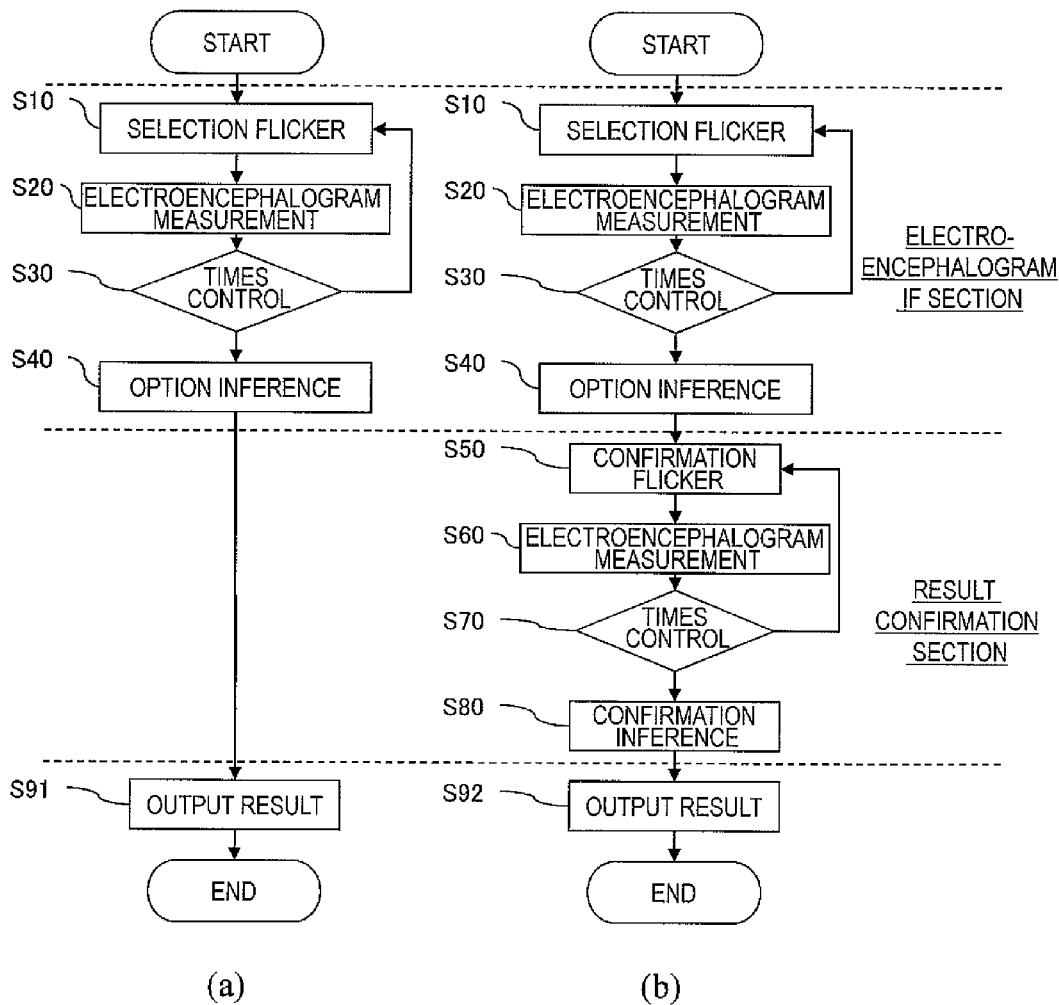

Portion (a) of FIG. 3 is a flowchart showing a procedure of processing by a conventional electroencephalogram interface system; and portion (b) of FIG. 3 is a flowchart showing a procedure of processing by the electroencephalogram interface system 1 of the present embodiment.

Portion (a) of FIG. 4 is a diagram showing an exemplary menu screen 21 which is displayed when an electroencephalogram interface is activated; and Portion (b) of FIG. 4 is a diagram showing waveforms 24a to 24d of event-related potentials of electroencephalogram signals, measured based on the flickering of each option as a starting point.

Figure 5:
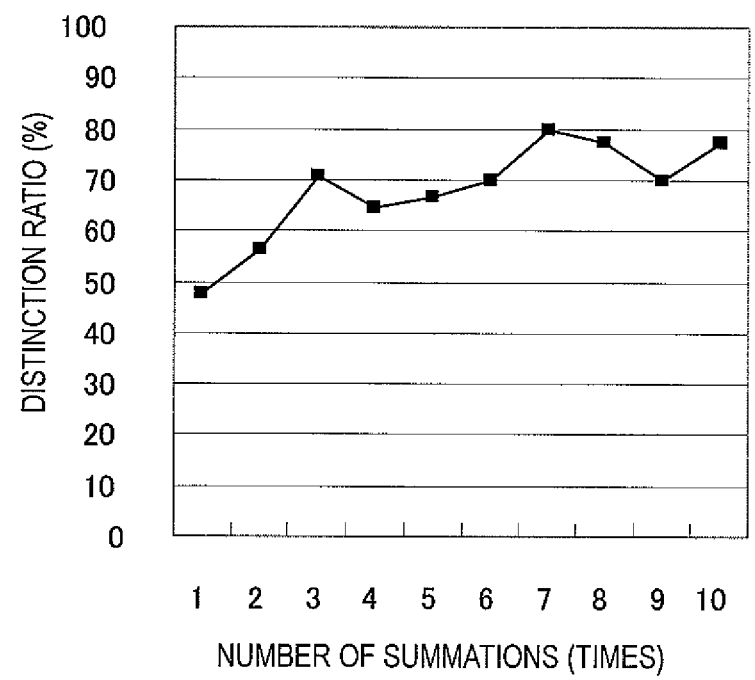

FIG. 5 is a diagram showing a relationship between the number of summations and the distinction accuracy (distinction ratio) in an experiment conducted by the inventors, where the electroencephalogram interface described in FIG. 4 was employed.

Figure 6A:
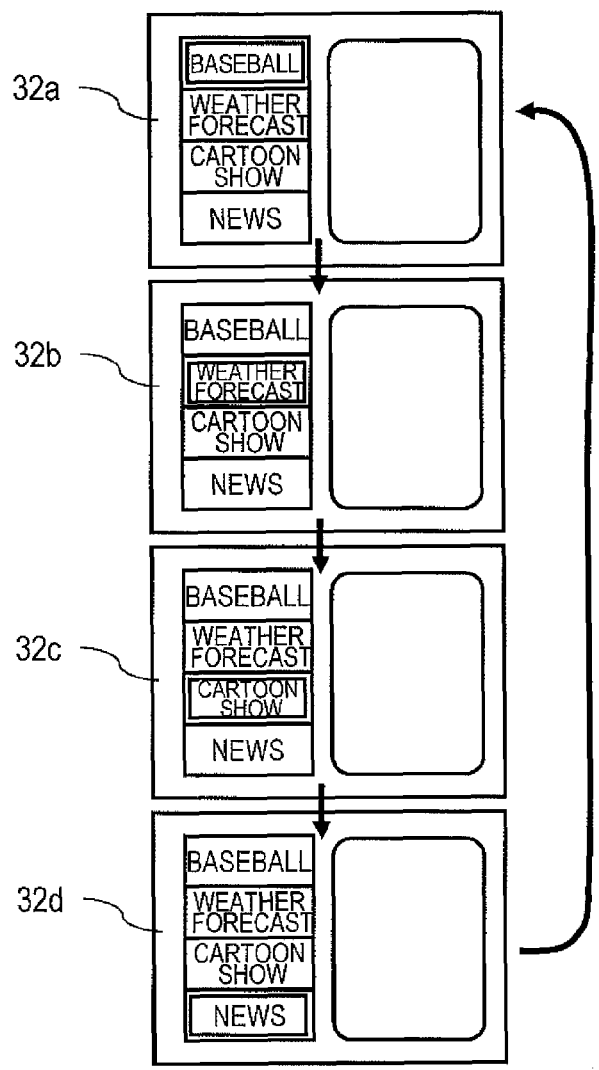
Figure 6B:
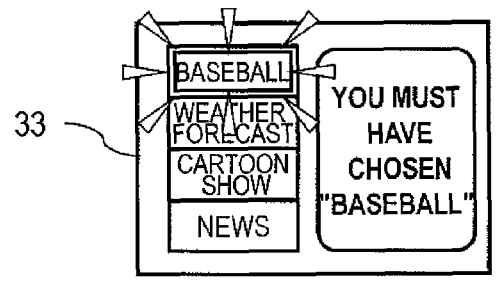

FIGS. 6A and 6B are diagrams showing screen images of an electroencephalogram interface system 1 according to Embodiment 1, where confirmation flickering is involved.

FIG. 7 is a diagram showing comparative results, against a conventional method, of the amount of time required until an option is determined in an electroencephalogram interface.

Figure 8:
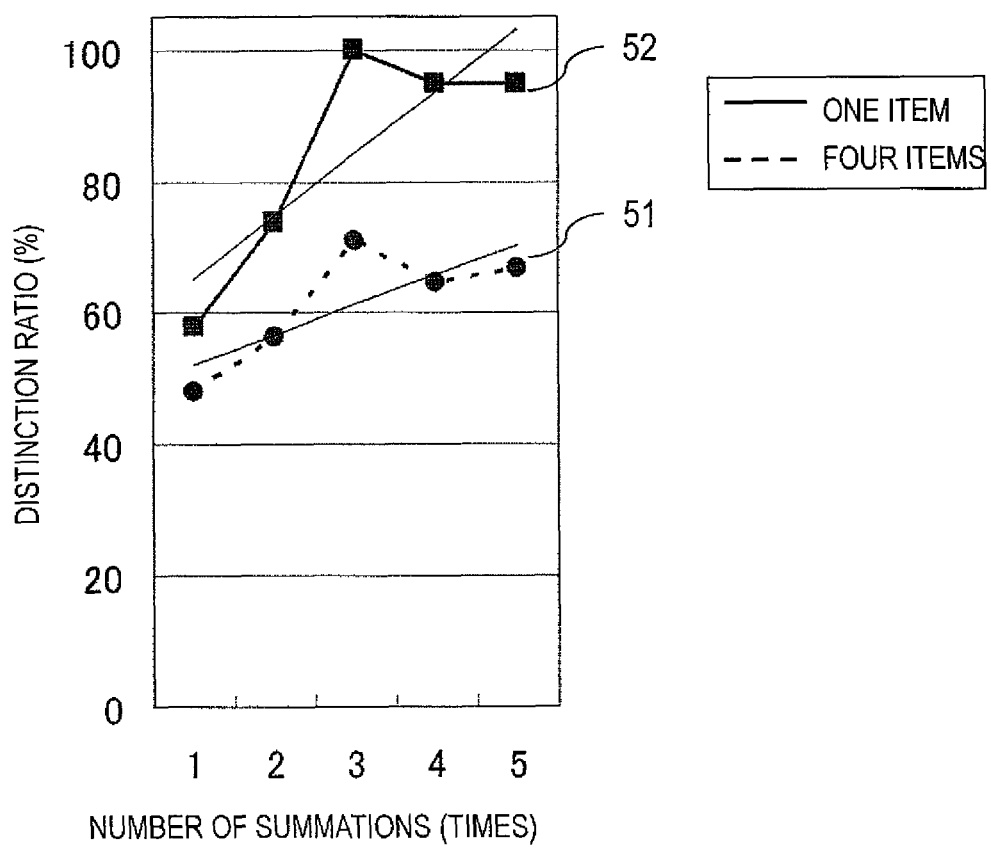

FIG. 8 is a diagram showing differences in accuracy of selection determination and confirmation determination depending on the number of summations.

Figure 9:
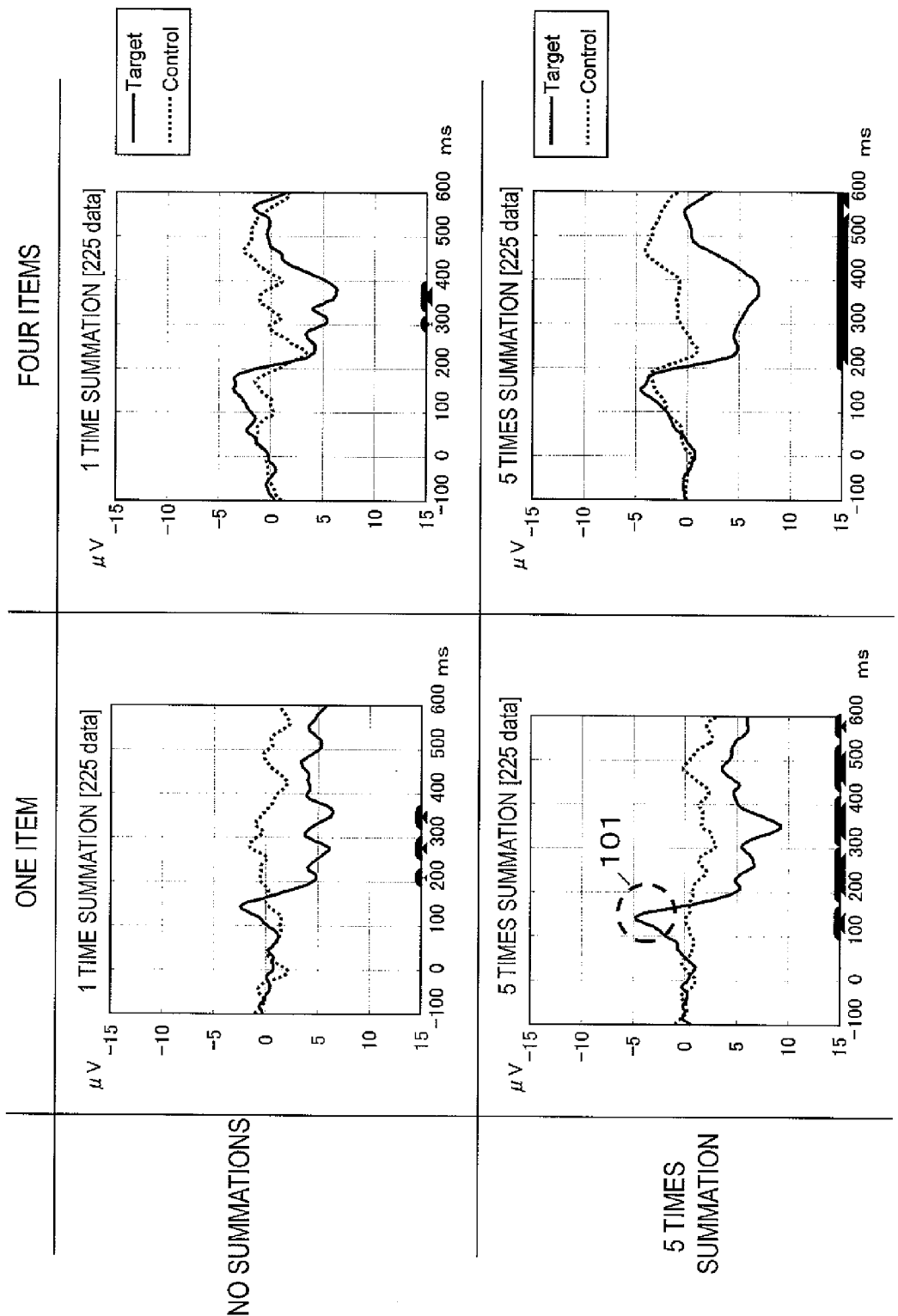

FIG. 9 is a diagram showing results of comparing event-related potentials for a condition to be extracted (Target) and event-related potentials for a condition not to be extracted (Control) to examine presence or absence of any significant difference.

Figure 10:
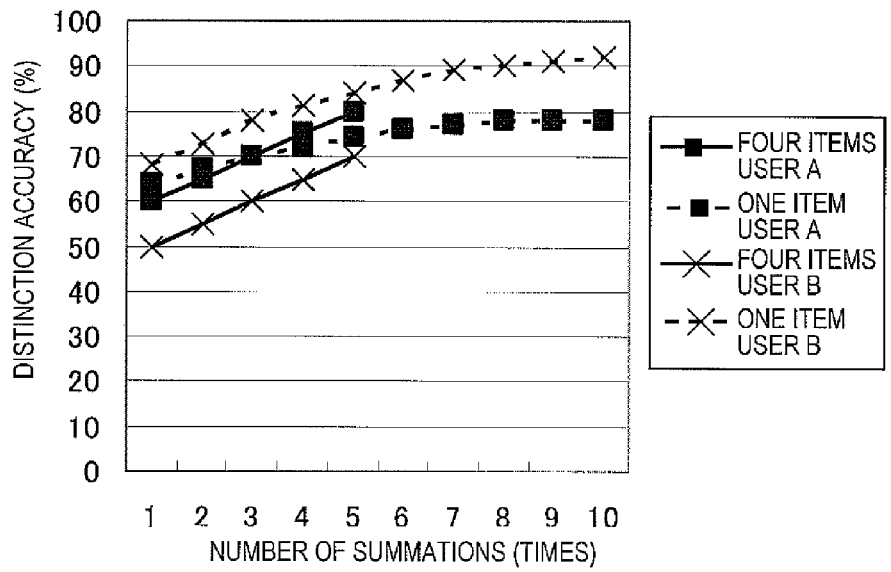

FIG. 10 is a diagram showing exemplary individual differences in distinction accuracy.

Figure 11:
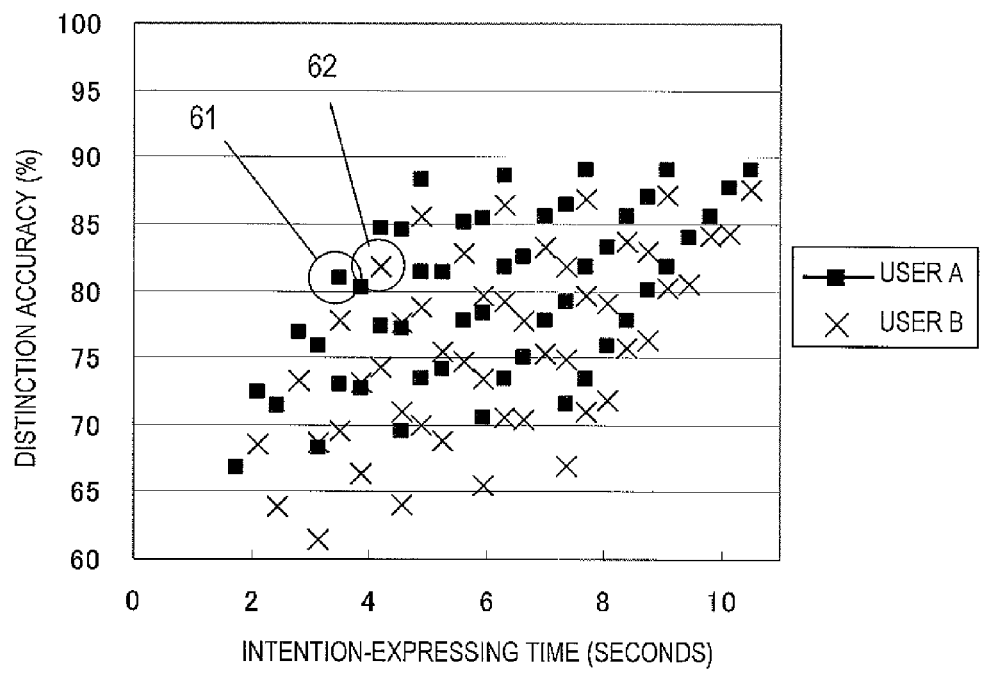

FIG. 11 is a diagram showing a distribution of intention-expressing time and distinction accuracy with various combinations of number of flickers in regard to each of user A and user B.

Figure 12:
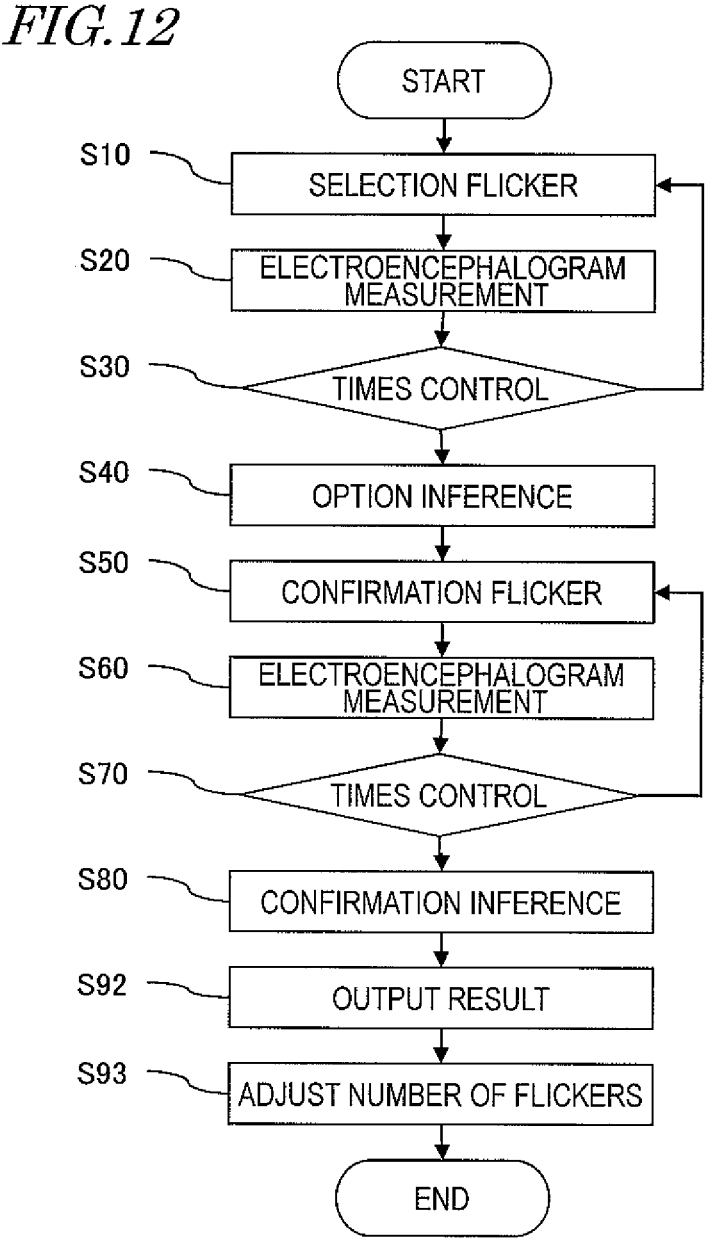

FIG. 12 is a flowchart showing a procedure of processing by an electroencephalogram interface system 1 according to Embodiment 2.

Figures 13A, 13B:
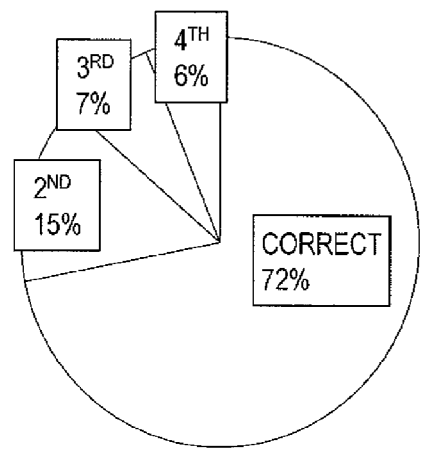

FIG. 13A is a diagram showing analysis results of experimental data with the electroencephalogram interface system 1; and FIG. 13B is a diagram showing results of studying effects of correction on the basis of the experimental data of FIG. 13A.

Figure 14:
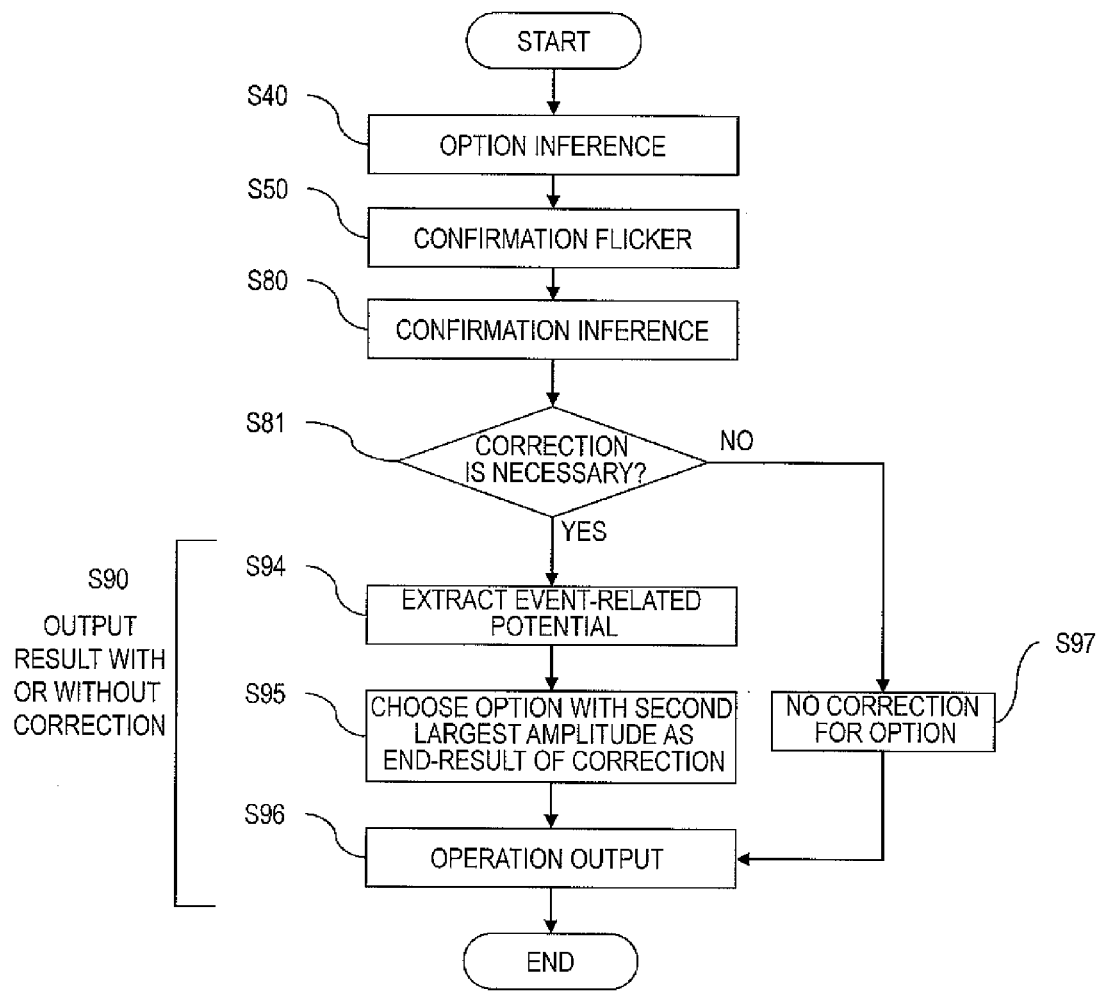

FIG. 14 is a flowchart showing a procedure of incorrect inference detection and option correction.

Figure 15:
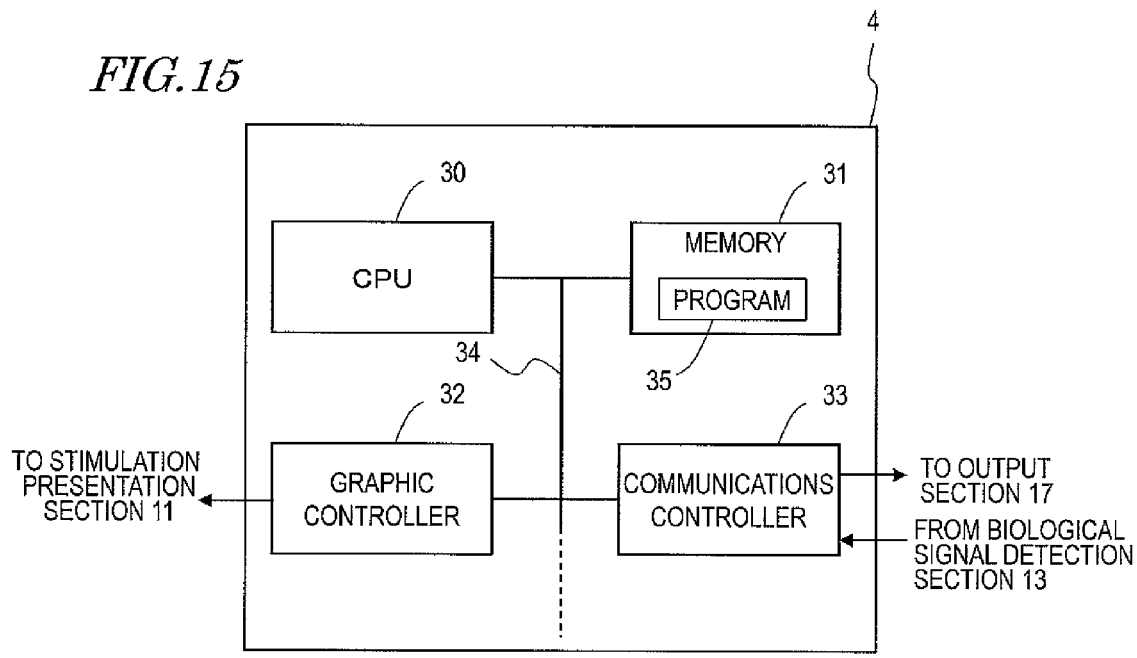

FIG. 15 is a diagram showing the hardware construction of an electroencephalogram IF providing apparatus 4.

Figure 16:
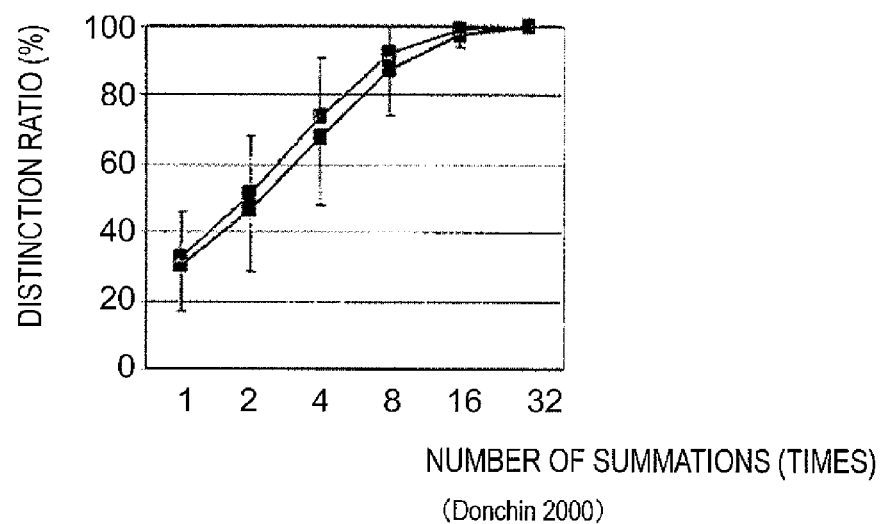

FIG. 16 is a diagram showing the number of summations for an event-related potential and the distinction ratio in an electroencephalogram interface.

DETAILED DESCRIPTION OF PREFERRED EMBODIMENTS

The inventors have taken note of the following two points to arrive at the electroencephalogram interface system according to the present invention.

Firstly, the inventors have paid attention to the response of a user when the user's desired option is incorrectly inferred. Such incorrect inferences are considered to occur no matter how the method of distinction is improved. As a result, the inventors have found that an incorrect inference can be identified from an event-related potential of the user. Specifically, the electroencephalogram interface system infers an option by utilizing an electroencephalogram of the user, and thereafter causes the inferred option to flicker for measuring an event-related potential that is contained in the electroencephalogram of the user. Then, by utilizing a signal component, e.g., the P300 component, of the event-related potential described later, it is possible to confirm whether the inferred option is the intended option or not. As a result, the inference accuracy can be improved.

Secondly, the inventors have found that, when the resultant option of inference is flickered for confirming whether the inference result is indeed the user's intended option or not, the number of flickers can be efficiently reduced. In the case where all options are to be flickered for inferring an option, if the number of flickers for each option is increased by one time, then the overall number of flickers will be increased by the number of options. However, in the case where only the inferred option is flickered for confirming the user's intent, the total increase incurred in the number of flickers will be only the one flicker which is additionally incurred for the option that is the result of inference. Therefore, the amount of time required after the user's intent is inferred and before the inference is determined as incorrect can be reduced.

As a result of these, an electroencephalogram interface system can be obtained which is able to confirm, after a user's intent has been inferred, whether that inference is correct or not. Then, if the inference is confirmed to be incorrect, the result of confirmation can be utilized for a retrial of the inference or correction of the option.

Hereinafter, with reference to the attached drawings, embodiments of the electroencephalogram interface system according to the present invention will be described.

Embodiment 1

The inventors envisage that, in future, an electroencephalogram interface system will be constructed in an environment in which a wearable-type electroencephalograph and a wearable-type display are combined. The user will be wearing the electroencephalograph and the display, and perform content viewing and screen manipulation by using the wearable-type display. Otherwise, it is envisaged that a brainwave interface system will be constructed in an environment (e.g., home) in which a home television set and a wearable-type electroencephalograph are combined. When watching television, the user is able to perform content viewing and screen manipulation by using an electroencephalogram interface, while wearing the electroencephalograph.

As used herein, an "electroencephalogram interface" means an interface which infers an intent of a user based on his or her electroencephalogram, and expresses this intent to a device to cause the device to be manipulated. In the electroencephalogram interface, there is a mapping between the electroencephalogram of the user and the user's intents (device manipulations), which allows a device manipulation that is desired by the user to be inferred from the electroencephalogram of the user.

Figure 1:
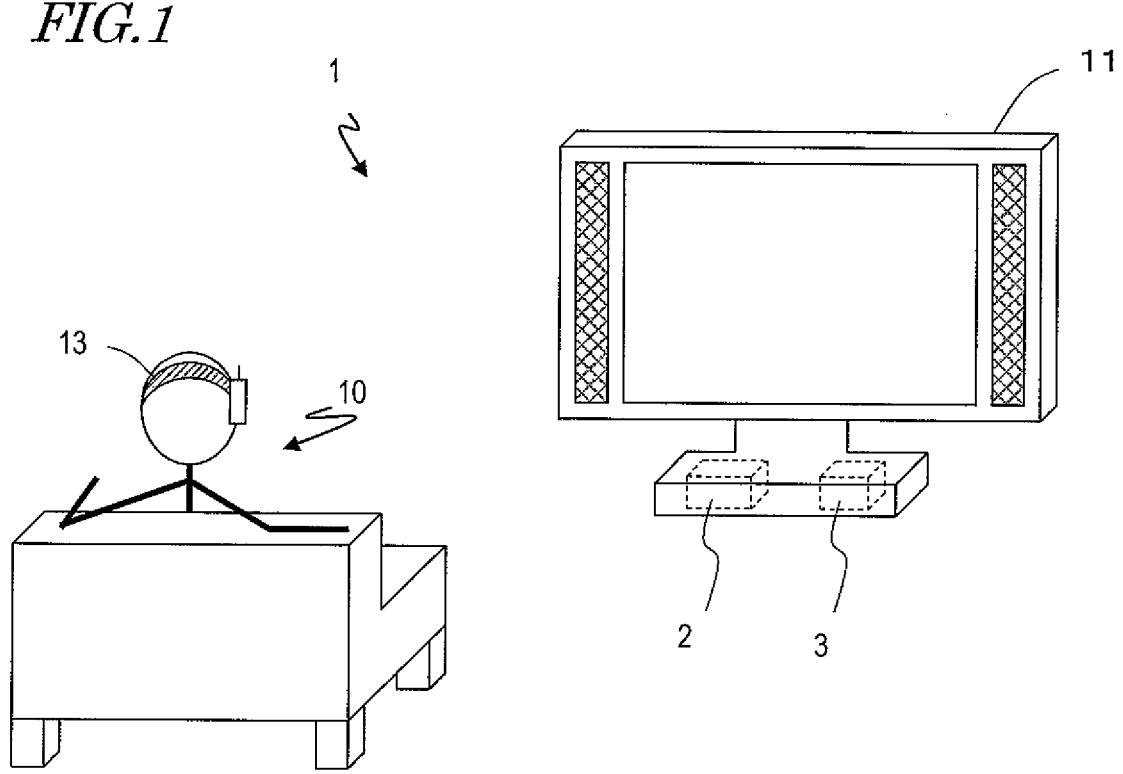
FIG. 1 is a diagram showing a construction and an environment of use for an electroencephalogram interface system 1 as contemplated by the inventors in an example where a television set for household use is utilized.

For example, FIG. 1 illustrates a construction and an environment of use for the electroencephalogram interface system 1 as envisaged by the inventors, in an example where a home television set is utilized. The electroencephalogram interface system 1 is exemplified so as to correspond to an electroencephalogram interface system construction of Embodiment 1 described later.

The electroencephalogram interface system 1 is a system for providing an interface for manipulating a TV 11 by utilizing an electroencephalogram signal from a user 10. An electroencephalogram signal from the user 10 is acquired by a biological signal detection section 13 which is worn on the head of the user, and transmitted to an electroencephalogram interface section 2 (also denoted as the "electroencephalogram IF section 2") in a wireless or wired manner. The electroencephalogram IF section 2 internalized in the TV 11 recognizes an intent of selection of the user by utilizing a P3 component of an event-related potential which constitutes a part of the electroencephalogram (the P3 component refers to a component of an event-related potential at around 300 ms from a starting point in the electroencephalogram, the starting point being a point in time at which a given event occurs, and is also referred to as the "P300 component"). It performs operations such as channel switching.

A result confirmation section 3 performs a process for confirming whether the inference result by the electroencephalogram IF section 2 actually matches the desire of the user or not. Then, if it is determined that the user's intent has not been properly inferred, the result confirmation section 3 makes a correction of the inferred option, or allows the user to again select an option by using an electroencephalogram interface. As a result of this, the user's intent will always be accurately expressed to the electroencephalogram interface system 1.

Next, the construction of the electroencephalogram interface system 1 will be described.

Figure 2:
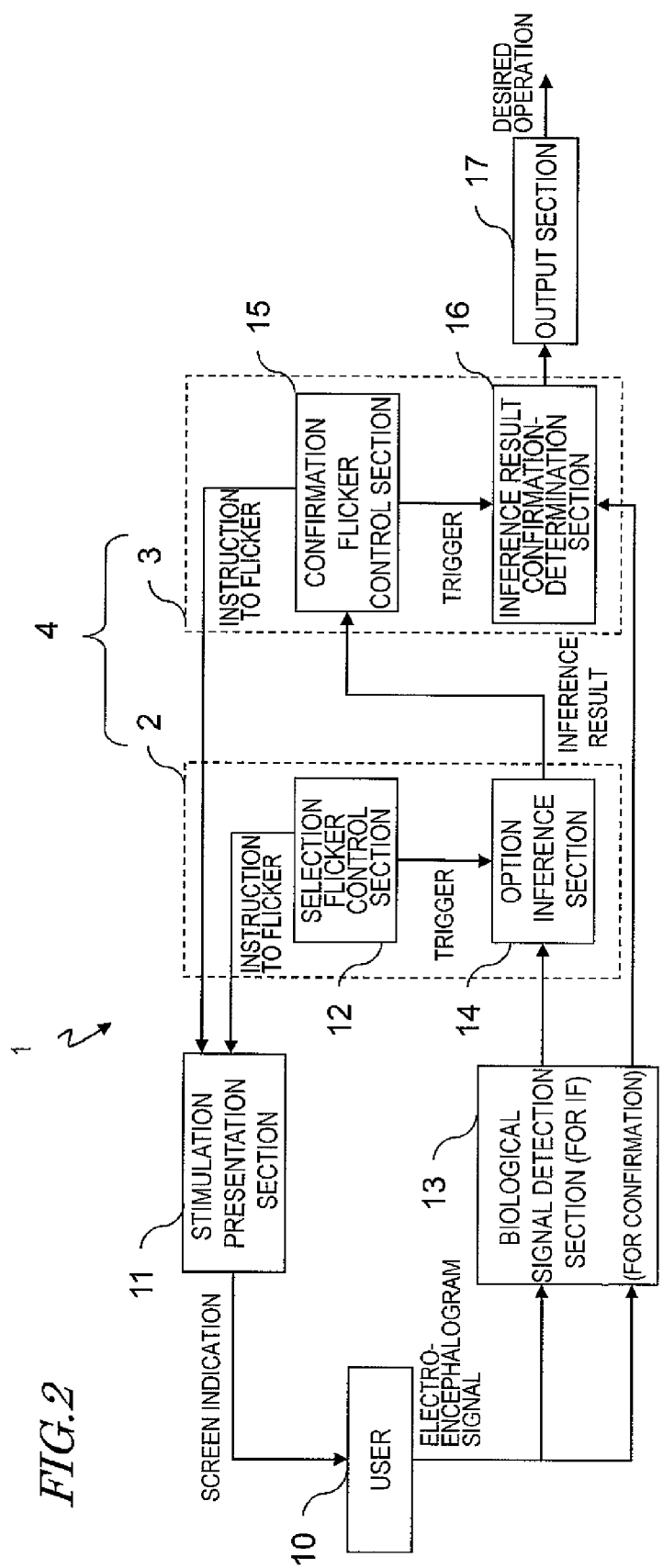
FIG. 2 is a construction diagram of an electroencephalogram interface system 1 according to an embodiment of the present invention.

FIG. 2 is a construction diagram of the electroencephalogram interface system 1 of the present embodiment.

The electroencephalogram interface system 1 includes the electroencephalogram IF section 2, the result confirmation section 3, a stimulation presentation section 11, the biological signal detection section 13, and an output section 17.

To the user 10 manipulating a device, the stimulation presentation section 11 presents options constituting an interface, a visual stimulation for confirmation's sake, and the like. For example, the stimulation presentation section 11 may be a television set, a display, or the like. The TV set shown in FIG. 2 functions as, and therefore is indicated by the same reference numeral as, the stimulation presentation section 11.

The biological signal detection section 13 is an electroencephalograph, for example, and measures changes in potential at an electrode which is worn on the head of the user. The measured changes in potential are the electroencephalogram signal from the user 10. The biological signal detection section 13 acquires the electroencephalogram signal from the user 10, and transmits the acquired electroencephalogram signal to the electroencephalogram IF section 2 in a wireless or wired manner. On the other hand, at the time of confirming the inferred intent of the user 10, the biological signal detection section 13 transmits the acquired electroencephalogram signal to the result confirmation section 3.

The outline of the operations of the electroencephalogram IF section 2 and the result confirmation section 3 is as already described above. Note that the electroencephalogram IF section 2 and the result confirmation section 3 may be implemented as a single apparatus. Such an apparatus will be referred to as an electroencephalogram interface providing apparatus 4 (also denoted as the "electroencephalogram IF providing apparatus 4") in the present specification.

The output section 17, which is the device to be manipulated, may be a display, for example. In the case of a display, it may also serve as the stimulation presentation section 11. Alternatively, the output section 17 may be a device (e.g., a remote control) which transmits an instruction signal to a device to be manipulated for instructing it to perform an operation corresponding to the inference result.

Hereinafter, the construction of the electroencephalogram IF section 2 and the result confirmation section 3 will be described in more detail.

The electroencephalogram IF section 2 includes a selection flicker control section 12 and an option inference section 14.

The selection flicker control section 12 controls the stimulation presentation section 11 with respect flickering of a plurality of options. The option inference section 14 (hereinafter referred to as the "inference section 14") analyzes the electroencephalogram signal measured by the biological signal detection section 13, and based on the analysis result, infers the option in the electroencephalogram interface which the user wishes to select.

The result confirmation section 3 includes a confirmation flicker control section 15 and an inference result confirmation-determination section 16.

When presenting the inference result on the stimulation presentation section 11, the confirmation flicker control section 15 displays, with flickering, the one option which is the inference result. The flickering of the inferred option, which is made for the purpose of confirming whether it is correct or not, is referred to as "confirmation flickering" in the present specification.

Within the electroencephalogram measured by the biological signal detection section 13, the inference result confirmation-determination section 16 (hereinafter referred to as the "determination section 16") analyzes the potential (event-related potential) of an electroencephalogram signal that is related to the confirmation flickering, thus determining whether the option that is being confirmation-flickered matches the option which is desired by the user.

The output section 17 executes a process which is in accordance with the result of confirmation by the determination section 16, and outputs its result. Specifically, if the determination section 16 that the option that is being confirmation-flickered matches the option which is desired by the user, the output section 17 executes an operation corresponding to that option. This is "output" as an operation result (e.g., channel switching) of the device desired by the user. On the other hand, if the determination section 16 determines that the option that is being confirmation-flickered does not match the option which is desired by the user, the output section 17 issues an instruction for a retrial.

Next, with reference to FIG. 3, the common processes and the differing processes between the conventional electroencephalogram interface system and the electroencephalogram interface system 1 of the present embodiment will be described. FIG. 3(*a*) is a flowchart showing a procedure of processing by the conventional electroencephalogram interface system, and FIG. 3(*b*) is a flowchart showing a procedure of processing by the electroencephalogram interface system 1 of the present embodiment.

The processes that are common to the conventional technique and the present embodiment are steps S10 to S40. The processes that differ between the conventional technique and the present embodiment are steps S50 to S80 being additionally performed in the present embodiment.

The conventional electroencephalogram interface infers a desired option from among the options, based on an electroencephalogram. On the other hand, in the electroencephalogram interface of the present embodiment, after a desired option is inferred from among the options based on an electroencephalogram, there is an additional process of confirming the resultant option of inference by the system for determining whether the inference result is correct or not.

First, the processes common to the conventional electroencephalogram interface system and the electroencephalogram interface system 1 of the present embodiment shown in portions (a) and (b) of FIG. 3 will be described in correspondence with the flow of processes in the electroencephalogram interface system of FIG. 4. In the following description, it is assumed that the respective component elements of the electroencephalogram interface system 1 shown in FIG. 2 perform the processes shown in FIG. 3(*b*).

At step S10, the selection flicker control section presents an option to the user 10 by flickering the option. The stimulation presentation section 11 includes an apparatus for presenting a visual stimulation to the user, e.g., a display, and after displaying a menu in which currently selectable options are listed, causes an option to be flickered.

Portion (a) of FIG. 4 shows an example of a menu screen 21 which is displayed when an electroencephalogram interface is activated. On the screen, a question 22 that says "Which program do you wish to watch?", and options 23*a* to 23*d* which are candidates of a program that may be being desired for watching, are presented. The options 23*a* to 23*d* are the following four: "baseball", "weather forecast", "cartoon show", and "news". One of these four is highlighted in a bright color. For example, "baseball" 23*a* is highlighted in the screen 21.

As used herein, an "option" is a menu (manipulation) item concerning a device manipulation. In the case of a TV set, for example, channels may be the manipulable items. In the case of an HDD recorder, record, playback, and so on may be the manipulable items. In other words, any manipulation to occur on a device for which an instruction is given by using a remote control or by the user directly touching the device, may be a manipulable item.

"Flickering of an option" refers not only to the option repetitively taking a visible state and an invisible state, but also to repetitive highlighting and unhighlighting of an option, for example.

"Highlight" is an indication using a background which is brighter than any other item, an indication in a bright text color, or an indication via pointing with a cursor or the like. In other words, highlighting means an attention-drawing indication.

Flickering of an option may be achieved by alternation of a state of drawing the attention of the user and a state of not drawing the attention of the user. It suffices if the option is indicated in such a manner that the user 10 looking at it will know which item the electroencephalogram interface system 1 is currently demanding attention of the user 10 to.

In the electroencephalogram IF section 2, at the time an option which he or she wants to select becomes highlighted, the user 10 focuses on the thought "I want to select it!". This thought appears as a change in the waveform of the electroencephalogram signal, and is measured by the biological signal detection section 13 at the next step.

At step S20, the biological signal detection section 13 begins measuring an electroencephalogram signal before each option becomes highlighted at step S10, and stores an electroencephalogram signal of a certain time slot containing the point of highlighting to a memory area in a memory (not shown), the memory area corresponding to each option.

Based on the point in time corresponding to the moment at which a highlight indication is made at step S13, the biological signal detection section 13 acquires an electroencephalogram signal in a time slot from e.g. 200 milliseconds before and until 1 second after that point in time. This electroencephalogram signal is utilized as an event-related potential. Stated otherwise, the electroencephalogram signal contains the event-related potential.

By utilizing the aforementioned event-related potential, the user's response to the highlighted item is obtained.

Each time receiving an electroencephalogram signal from the biological signal detection section 13, the electroencephalogram IF section 2 stores it to a memory (not shown). By storing each electroencephalogram signal in a memory area corresponding to each option, it is possible to make a waveform comparison between the respective options, for use in the inference of options or the like.

Note that the biological signal detection section 13 does not need to have a memory. The biological signal detection section 13 may keep outputting electroencephalogram signals, and the electroencephalogram IF section 2 may keep storing the electroencephalogram signals and cut out the aforementioned electroencephalogram signal that is needed.

Herein, the starting point of an event-related potential is not limited to the point in time at which an option becomes highlighted, but may be the point in time at which an option becomes unhighlighted. Thus, in the present specification, the expression "flickering of an option is used as a starting point" is employed to refer to any of the following starting points: the point in time at which an option becomes highlighted; the point in time at which an option becomes unhighlighted; the point in time at which an option becomes displayed; and the point in time at which an option becomes undisplayed.

At step S30, the selection flicker control section 12 controls selection flickering. "Selection flickering" is flickering of an option which is made in order to allow the user to select an option, which is a device manipulation menu item. The selection flicker control section 12 performs control as to which option is to be highlighted, when an option is to be highlighted, how many times each option is to be highlighted, and so on. As shown in portion (a) of FIG. 4, the selection flicker control section 12 first selects the topmost option, i.e., "baseball" 23*a* for flickering. Then, each time this step S30 is executed, a next option is consecutively selected for flickering, until wrapping around to the topmost baseball after fourth, i.e., "news" 23*d*.

In the electroencephalogram interface system 1, in the case where noise is often contained in each single waveform because of fluctuations of the electroencephalogram waveform, a process of extracting a necessary signal through arithmetic mean is performed to solve this situation. This number of repetitions is set to 5 times or 10 times, for example; and each option is highlighted a plurality of times, and an arithmetic mean of the responses (electroencephalograms) thereof is taken so as to be used in the signal distinction. This number of repetitions is determined based on the state of the electroencephalogram, the state of the individual's waveform, the determination accuracy, and the like; it may possibly be 1 time, without involving any summation (no summations).

Although step S30 of the present embodiment is illustrated as highlighting items consecutively, a method of random highlighting may also be possible. This will make it unknown which items are going to be highlighted in what order in advance, thus leading to a possibility that the menu selection may be made more carefully.

At step S40, the inference section 14 infers the option which the user 10 wishes to select. Specifically, the inference section 14 infers the option by comparing the event-related potential for each option as measured and stored by the biological signal detection section 13 against the waveform of a predetermined characteristic component. For example, portion (b) of FIG. 4 shows waveforms 24*a* to 24*d* of event-related potentials of electroencephalogram signals, measured based on the flickering of each option as a starting point. A characteristic component is only observed in the waveform 24*b* here. The inference section 14 prestores waveform information which makes this characteristic component distinguishable. The inference section 14 compares the waveform of each obtained event-related potential against the waveform of the predetermined characteristic component, and determines an option which has the predetermined characteristic component. "An option having the predetermined characteristic component" should also encompass any option with a waveform which has a high similarity level to the waveform of the predetermined characteristic component. Next, the inference section 14 infers that the option that the user 10 wants to select is the option corresponding to the waveform 24*b*, i.e., "weather forecast" 23*b*, which has the waveform of the characteristic component.

For the comparison, a visual P3 component of an event-related potential can be used, for example. A "visual P3 component" refers to a component of an event-related potential having a positive (plus-direction) peak in its amplitude, in an electroencephalogram signal from 200 milliseconds to 400 milliseconds based on an event which stimulates the visual sense (flickering of an option) as a starting point. Note that "having a positive peak in amplitude" only requires having a local maximum, which is inclusive of a maximum value. Alternatively, the inference section 14 may compare the peak amplitude levels at 300 milliseconds±50 milliseconds. For example, an option which is associated with a waveform having the largest peak amplitude level may be inferred as the option desired by the user. Moreover, the inference section 14 may generate a template from a typical P300 waveform which is prepared in advance, calculate similarity levels with that template, and infer an option based on its similarity level. For example, an option which is associated with a waveform having a large similarity level with the template may be inferred as the option desired by the user.

At step S92, the inference section 14 in the electroencephalogram interface system 1 of the present embodiment outputs an option which is presumably what the user wants to select, to the next step. In the conventional process, at step S91, the resultant option of inference would be displayed on a screen or the like, and an operation described for the option would be executed.

Through the above processes, with the electroencephalogram interface system 1, an option which is intended by the user 10 can be inferred from an event-related potential of the electroencephalogram, without requiring button manipulations or the like.

In order to enhance the accuracy of this inference, a possible method may be to perform a whole round of flickering of the respective options in plural trials, and take a sum of the event-related potentials measured based on the flickering of each option as a starting point. The inventors have conducted the following experiment, and confirmed its effectiveness.

FIG. 5 shows a relationship between the number of summations and the distinction accuracy (distinction ratio) in an experiment conducted by the inventors, where the electroencephalogram interface described in FIG. 4 was employed. Although some fluctuations were observed because of the small number of test subjects and the small number of repetitions in the experiment, the trend can be generally summarized as follows. First, when the number of summations (on the horizontal axis) was 1 to 3 times, the distinction ratio was about 50% to 60%. When the number of summations was 8 to 10 times, the distinction ratio improved to 70% to 80%. In other words, a positive correlation was found between the number of summations and the distinction ratio.

In order to obtain a highly accurate distinction ratio, a sufficient number of summations of e.g. 10 to 20 times would presumably be required. However, increasing the number of summations would result in a long presentation time. This point has already been described in relation to the problems to be solved by the invention.

Therefore, in view of this problem, the inventors have considered the use of an electroencephalogram when the user's desired option is incorrectly inferred. Such incorrect inferences are considered to occur no matter how the method of distinction is improved. The inventors have realized that, even if the electroencephalogram IF section 2 fails to correctly infer the user's desired option, the correctness/incorrectness of the inference can be identified from an event-related potential of the user. Specifically, in a manner similar to when the user selects an option, the resultant option of inference may be flickered, and an event-related potential may be measured based on the flickering as a starting point and its component such as P300 be analyzed, thus enabling a determination of the user's will concerning the confirmation as to whether the inference result was correct or not.

By paying attention to this, the inventors have arrived at the concept of allowing the electroencephalogram interface system 1 to additionally perform steps S50 to S80 shown in FIG. 3(b).

Hereinafter, a flow of confirmation processes from steps S50 to S80 in FIG. 3(b) will be described with occasional reference to FIGS. 6A and 6B. FIG. EA shows an example of switching the option indication in connection with the flow of processes of steps S10 to S30 in FIG. 3.

Step S50 is a process of presenting a stimulation for confirmation by allowing the resultant option of inference to be flickered to the user 10. The stimulation presentation section 11 presents a stimulation. For example, as shown in an exemplary indication of the inference result in FIG. 6B, a message "You must have chosen 'baseball'" is indicated, and also the "baseball" option becomes highlighted, after which flickering is begun.

For this flickering at step S50, if the user's desired option fails to be presented as the resultant option of inference, the user will watch the menu while thinking "That's not right" when the option for confirmation becomes highlighted. This will is reflected in his or her event-related potential, and expressed to the result confirmation section 3 in the subsequent steps.

On the other hand, for the flickering at step S50, if the user's desired option is indeed correctly presented as the resultant option of inference, the user ends the confirmation task. In this case, the user does not need to think "Yes", "Yes, that's it", and so on. What is necessary is the fact that the user has consciously confirmed the incorrectness of the inference result. Therefore, when the inference result is correct, the user does not need to have any particular thought with respect to the confirmation flickering; on the other hand, when the inference result is incorrect, the user is supposed to think "That's not right" for the inference result, thus enabling a distinction between the two cases.

At step S60, the biological signal detection section 13 measures an electroencephalogram signal in a certain time slot containing the point in time at which the option for confirmation becomes highlighted at step S50, and stores it to a memory. Specifically, based on the point in time corresponding to the moment at which a highlight indication is made at step S50, the biological signal detection section 13 acquires an electroencephalogram signal from 200 milliseconds before to 1 second after that point in time. As a result of this, an event-related potential contained in the electroencephalogram signal is acquired, whereby the user's response to the highlighted option for confirmation is obtained.

At step S70, the confirmation flicker control section 15 controls the flickering period and the number of times of confirmation flickers. The confirmation flicker control section 15 performs highlighting and unhighlighting of the option for confirmation (confirmation flickers) with a predetermined period. The confirmation flicker control section 15 counts the number of flickers. Then, if the number has not reached a predetermined number of flickers (e.g., 10 times), the process returns to step S50 to perform flicker control; if the predetermined number of flickers has been reached, the flicker control is ended, and the process proceeds to step S80.

At step S80, the determination section 16 determines the result of confirmation. The determination section 16 determines whether a characteristic component having the waveform which would occur in relation to confirmation is contained in the event-related potential of the electroencephalogram signal which is measured by the biological signal detection section 13 based on the confirmation flickering as a starting point. The determination section 16 prestores waveform information for enabling distinction of this characteristic component having the waveform which would occur in relation to confirmation. The determination section 16 compares the measured waveform of the event-related potential of the electroencephalogram signal against the waveform of the predetermined characteristic component, and determines whether the predetermined characteristic component is contained or not. For example, the determination section 16 determines whether the waveform of the event-related potential contains the predetermined characteristic component based on whether the measured waveform of the event-related potential of the electroencephalogram signal has a similarity level which is equal to or greater than a predetermined threshold value to the waveform of the predetermined characteristic component. Then, based on the result of determination, the determination section 16 determines whether the desired option has been presented or not. For example, if the waveform of the event-related potential has a similarity level equal to or greater than the predetermined threshold value, the determination section 16 determines (infers) that the waveform contains the predetermined characteristic component, and that the option corresponding to the desired manipulation of the user has been presented. On the other hand, if the waveform of the event-related potential has a similarity level which is smaller than the predetermined threshold value, the determination section 16 determines (infers) that the waveform does not contain the predetermined characteristic component, and that the desired option has not been presented.

More than one method will be possible for determining whether the waveform component which would occur in relation to confirmation is contained in the event-related potential or not. For example, the time (latency) of the apex of a reversed (i.e., pointing in the positive direction) hill-shaped waveform may be subjected to a comparison to determine a match or a non-match, or the summed waveform of portion (b) of FIG. 4 may be stored as a template and the shapes of the summed waveform and the template may be compared to determine a match or a non-match. As a result, an incorrect inference by the system can be detected, whereby the need for correcting the inference result can be determined. Herein, the time (latency) of an apex of a reversed hill-shaped waveform can be defined as, in the case of confirming P300, for example, a point in time of the largest value in an event-related potential which exhibits a positive change between 200 milliseconds and 400 milliseconds since the confirmation flickering.

If this latency greatly differs from the reference value, it can be determined that no signal resulting from confirming the inference result is contained.

At step S92, the determination section 16 outputs this inference result. If the inference result is correct, an instruction to execute an operation corresponding to the option is issued: e.g., in the case of a television set, changing the content of the screen indication. Note that the output may vary depending on the functions that are provided by the interface.

Through the confirmation processes from steps S50 to S80 as such, even if an incorrect inference is made in the option inference process, the incorrectness of the inference can be identified.

This confirmation step provides an effect of performance improvement while maintaining the overall distinction ratio. This will be described with reference to FIG. 7.

FIG. 7 shows comparative results, against the conventional method, of the amount of time required until an option is determined in an electroencephalogram interface. These results are described in terms of the number of flickers, the time required until all flickers are completed (selection/determination time), and the time during which it is necessary to watch flickering to express an intent (intention expressing time). In the calculations of the values in the table, the number of options was 4 and the flicker interval was 350 milliseconds, and two conventional cases were considered: one where the number of flickers was 5 times, and another where the number of flickers was 10 times. Regarding the assumptions of accuracy, the numerical values from FIG. 5 (66.7% for 5 times summation, 77.5% for 10 times summation) were taken, and equivalent numerical values were used for the relationship between the number of summations and the accuracy with respect to flickering of each option and the relationship between the number of summations and the accuracy with respect to confirmation flickering.

With reference to FIG. 7, conventional method A, where the number of flickers for each option is set to 5 times, will be described first. In conventional method A, the total number of flickers is 20 times, and the flicker interval is 350 milliseconds, and thus the time required for selection/determination 43 is 20 times*350 milliseconds=7 seconds. Since there is no confirmation process, the intention-expressing time 44 is the same 7 seconds, and the distinction accuracy is calculated to be 66.7% from the assumptions of FIG. 5.

In conventional method B, where the number of flickers for each option is 10 times, through similar calculations to those of conventional method A it follows that: the total number of flickers is 40 times; the time required for selection/determination is 14 seconds; the intention-expressing time is 14 seconds; and the distinction accuracy is calculated to be 77.5% from the assumptions of FIG. 5.

Next, calculations according to the method of the present invention, which combines selection flickering and confirmation flickering, will be described.

A case where the selection flickering is performed times and the confirmation flickering is performed 10 times will be considered. The total number of flickers is selection 5 times*4 options+confirmation 10 times=30 times. As for the selection/determination time, 20 times*350 milliseconds=7 seconds for the selection flickers, and times*350 milliseconds=3.5 seconds for the confirmation flickers, thus resulting in a total as small as 10.5 seconds.

As for the intention-expressing time, an intent to make a correction needs to be indicated only with regards to incorrect inferences; therefore, it is unnecessary to always be looking at the confirmation flickers, which results in a small intention-expressing time. For example, by employing the numerical values from FIG. 5, the distinction ratio is calculated to be 66.7% under 5 times summation. The cases where an intention for correction needs to be expressed at the time of confirmation account for 100%−66.7%=33.3%. Therefore, as for the average intention-expressing time, an average of about 1.2 seconds is needed for confirmation flickers, i.e., 3.5 seconds*33.3%.

Next, the distinction accuracy will be discussed. This is based on the assumptions that the distinction accuracy for an option through an arithmetic mean over 5 times is 66.7%, and that the distinction accuracy for 10 times of confirmation flickering is 77.5%. There are four possible situations based on the combinations of correctness of selection and correctness of confirmation.

When confirmation flickering is introduced as in the present embodiment, there will be situations where the selection happens to fail but a need for correction is recognized during confirmation, thus resulting in an improved final distinction accuracy; however, there will also be situations where a correct selection happens to be erroneously determined as requiring correction (i.e., "incorrect") during confirmation, and so on. Based on combinations of such plural situations, the total probability of arriving at a correct selection will presumably be 78.8%.

Thus, as will be understood from the table of FIG. 7, according to the present embodiment, the number of flickers for each option is decreased as compared to conventional method B, and yet the additionally-introduced confirmation flickers only account for a portion of the decrease. Thus, it is possible to maintain a high distinction accuracy while reducing the total flicker time.

In the example of FIG. 7, the allocation of the number of flickers is made with a view to reducing the intention-expressing time while maintaining the same level of distinction accuracy. On the other hand, confirmation flickering may be used for the purpose of improving the distinction accuracy. In this case, confirmation flickers may be added without decreasing the number of flickers for selection, whereby an improved distinction accuracy can be obtained over the conventional method.

In the present embodiment, the method of intent analysis for confirmation flickering utilizes a characteristic feature of the electroencephalogram concerning confirmation flickering which was newly discovered by the inventors. This establishes a different method from the analysis method for selection flickering, and provides for an improved performance over the analysis for selection flickering.

FIG. 8 shows differences in accuracy of selection determination and confirmation determination depending on the number of summations. In FIG. 8, the horizontal axis represents the number of summations, and the vertical axis represents the distinction ratio. A graph 51 shows accuracy of selection determination when a selection is made from among four options, whereas a graph 52 shows accuracy of confirmation determination when an intent is determined by watching an icon which is flickering alone. There are two differences between the two graphs: (1) the graph 52 shows a better distinction ratio as a whole; and (2) the graph 52 shows a steeper gradient of accuracy improvement in the distinction ratio, which means the effect of summation being more pronounced.

Presumably, the difference in the overall distinction ratio related to (1) above also contains effects of the difference in the number of options. When there are four options, a 25% accuracy would result from random inference; when there is one option, a 50% accuracy would result from random inference. That is, the difference in the number of options itself is reflected as a difference in the distinction ratio.

Presumably, the difference in the improvement in the distinction ratio related to (2) above is not any influence of the number of options, but is another factor. This factor is a difference in the electroencephalogram characteristics, which in turn is ascribable to a difference in the experiment conditions.

Hereinafter, results of an experiment and analysis conducted by the inventors on their own intent be described with reference to FIG. 9. The inventors measured electroencephalograms of 15 test subjects.

FIG. 9 shows results of comparing event-related potentials for a condition to be extracted (Target) and event-related potentials for a condition not to be extracted (Control) to examine presence or absence of any significant difference.

There are two conditions (tasks) for measuring an electroencephalogram. A first one is a task where four options are presented, among which one option is to be selected by using an event-related potential for selection highlighting thereof. A second one is a task where one icon is flickered, and a confirmation highlight is being watched while an event-related potential for the confirmation highlight is utilized. The results obtained under the first measurement condition are indicated as "four items" in FIG. 9. The results obtained under the second measurement condition are indicated as "one item" in FIG. 9.

For each of the 15 test subjects, 225 event-related potentials were randomly extracted for summation, with respect to each of the case of 1 time summation and the case of 5 times summation, thus ensuring an equal number of waveform data. A zone which exhibited a significant difference (1%) in the test is indicated by a thick line appearing at the bottom of the graph.

The zone with a significant difference is a zone which exhibits a clear difference between the electroencephalograms of the condition to be extracted and the condition not to be extracted, and this zone may be regarded as containing information for distinguishing electroencephalograms corresponding to both conditions. For example, in the one item/no summations graph, a zone with significant difference is observed at about 200 to 400 milliseconds, and therefore it is this zone that contains information for use in the distinction.

According to the graph of FIG. 9, in the case of performing no summations, the zone with a significant difference is broader in the graph of one item than in the graph of four items. This indicates that confirmation flickering contains more information, and accounts for the higher distinction ratio and greater improvement in the distinction ratio.

FIG. 9 shows an arithmetic mean waveform for a confirmation highlight with a single icon (the one item/5 times summation graph), which exhibits upward-projecting waveform 101 basically between 100 milliseconds and 200 milliseconds, this component being considered to contribute to the distinction ratio. This component is a component of the event-related potential called "N200", as will be described later.

As described above, according to the present embodiment, an electroencephalogram signal (event-related potential) is used not only for the inference of an option in an electroencephalogram interface, but also for confirming the correctness of the resultant option of inference. As a result, with a similar number of flickers, the amount of time required for a user to express his or her will can be reduced, thus enabling an efficient use of the electroencephalogram interface. Moreover, due to the newly recognized characteristics of the electroencephalogram signal with respect to the confirmation flickering, there is a higher distinction accuracy with respect to the confirmation flickering than with respect to the selection flickering, whereby a further improved efficiency is provided.

Embodiment 2

Embodiment 1 illustrates an overall operation of the electroencephalogram interface system.

In the present embodiment, an operation will be described in which the selection flicker control section 12 and the confirmation flicker control section 15 adjust the number of flickers in accordance with the operation status of the electroencephalogram IF section 2 and the operation status of the result confirmation section 3. The construction of the electroencephalogram interface system of the present embodiment is the same as in Embodiment 1. Therefore, only those component elements which have different functions from Embodiment 1 will be described, while omitting the descriptions of any component elements having the same functions as in Embodiment 1.

Due to time constraints on manipulating an electroencephalogram interface, it is preferable that the number of selection flickers and the number of confirmation flickers are as small as possible. However, the electroencephalogram interface needs to infer an item which a user wants to manipulate with a sufficiently high accuracy from the user's electroencephalogram. In order to satisfy both needs, it is considered effective to appropriately allocate the number of selection flickers and the number of confirmation flickers. In the meantime, it is expected that the optimum allocation of numbers must vary for each individual person. Hereinafter, a method of allocation will be described.

It is known that the electroencephalogram waveform has large individual differences, and that, for the same task, the electroencephalogram waveform to appear will vary from person to person. In the electroencephalogram interface of Embodiment 1, too, P300 (which is an evoked response for an intent of selection) was observed for selection flickering, whereas an evoked response for the flickering of a single option was observed for confirmation flickering. FIG. 9 also indicates that the evoked response even includes a component which occurs earlier than P300.

Thus, it is expected that each component has a different way of appearing in the electroencephalogram waveform depending on the individual person, thereby resulting in a different distinction accuracy and a different optimum number of flickers. A "distinction accuracy" refers to an accuracy with which a user infers a desired item from among a plurality of items. Hereinafter, this will be described with respect to an imaginary example.

FIG. 10 shows exemplary individual differences in distinction accuracy. Exemplary responses of user A and user B are shown, with respect to flickering of four menu items and flickering of one item. In FIG. 10, the horizontal axis represents the number of summations, and the vertical axis represents the distinction accuracy.

The evoked responses (1 time to 5 times summation) for four items indicated by solid lines in FIG. 10 show that the distinction accuracy for user A is higher than the distinction accuracy for user B. On the other hand, the evoked responses (1 time to 10 times summation) for one item indicated by dotted lines in FIG. 10 show that the distinction accuracy for user B is higher than the distinction accuracy for user A. This situation is possible because the distinction accuracies vary from individual person to individual person.

In this situation, if the number of selection flickers is varied from 1 time to 5 times and the number of confirmation flickers is varied from 1 time to 10 times, there emerges a total of 50 combinations. For each, estimations of a intention-expressing time and an assumed distinction accuracy as exemplified in FIG. 7 can be made.

FIG. 11 shows a distribution of intention-expressing time and distinction accuracy with various combinations of numbers of flickers in regard to each of user A and user B. The assumed conditions for the calculations are the same as in the calculations of FIG. 7. It can be seen from FIG. 11 that various intention-expressing times and distinction accuracies are expected for different combinations of number of flickers. It can also be seen that user A and user B span different ranges of distribution because of having different relationships between the number of times and the distinction accuracy. Such a distribution will vary depending on the number of times/accuracy graph of each user as shown in FIG. 10, and an optimum number of times can be set based on this distribution.

For example, in each distribution of FIG. 11, a combination that leads to the smallest intention-expressing time under a lowest assumed distinction accuracy of 80% is searched for. For user A, the assumed distinction accuracy is 80.9% and the intention-expressing time is 3.5 seconds when the number of selection flickers is 3 times and the number of confirmation flickers is 6 times. For user B, the assumed distinction accuracy is 81.8% and the intention-expressing time is 4.2 seconds when the number of selection flickers is 4 times and the number of confirmation flickers is 6 times. Thus, the optimum number of flickers varies from person to person. Therefore, it is possible to make a correction so as to approach the optimum number of flickers. Note that the lowest assumed distinction accuracy value of 80% is only an example; other numbers of flickers can be set by applying additional correction depending on the application, or other numbers of flickers can be set also by setting a largest tolerable intention-expressing time.

Based on this finding, it can be said that the optimum number of selection flickers and the number of confirmation flickers differ from user to user. Depending on the manner in which the user's waveform appears, the number of times, and accuracy improvements, adjustments can be made between increasing the number of selection flickers and increasing the number of confirmation flickers.

As a method for determining the numbers of flickers, if the degree of distinction accuracy improvement in response to an increase in the number of selection flickers or an increase in the number of confirmation flickers is known as in the above, distributions such as those of FIG. 11 can be generated, from which desired numbers of flickers can be determined. However, it might be a burden to determine a distinction rate for each user under ever condition. Hereinafter, other methods for determining numbers of flickers will be described.

A first method for determining numbers of flickers is a method utilizing a certainty level of inference at the time of selection. The certainty level is an index which indicates how certain an inferred option is to the user. The certainty level may take two states corresponding to "high" or "low", for example. Alternatively, the certainty level may be expressed in a numerical value. Since the inference section 14 compares the event-related potential waveforms for the respective options, it is possible to calculate a value as to how certain the inferred option is. For example, similarity levels are calculated between waveforms for the respective event-related potentials for four options. In this case, if only one waveform is clearly different from the other three waveforms, it can be said that there is a high certainty level.

Specifically, in the case of four options, the user presumably has an intent to select one of the four options. In this case, among the four event-related potential waveforms for the options, it can be considered that an electroencephalogram component concerning an intent of selection is contained only in the event-related potential for the desired option. An electroencephalogram component concerning an intent of selection may be, for example, an electroencephalogram component near 300 milliseconds, called P300. Under ideal measurement conditions, only one of the four event-related potentials will contain a P300 electroencephalogram component, and therefore a characteristic feature will be found only in the waveform for the desired option through inter-comparison between the four waveforms.

For example, assuming that the processing scheme by the inference section 14 adopts a method of retaining a standard template waveform concerning intents of selection and inferring an option through a comparison of similarity levels between the template waveform and the four event-related potentials, then, under ideal measurement conditions, it is expected that only one of the event-related potentials will have a high similarity level with the template waveform, while the other three event-related potentials will have low similarity levels alike. In this case, it can be said that there is a high certainty level.

On the other hand, if noise is mixed at the time of measurement, it may so happen that the waveforms of the four event-related potentials resemble the template waveform. In this case, since the desired option is not clear, confirmation needs to be carefully done.

The "similarity level" can be relied upon to determine whether the waveforms of the four event-related potentials resemble the template waveform or not. As a method of calculating the similarity level, a simple mean squared error between the waveform for comparison and the template waveform for respective sampling values may be used, or a correlation coefficient may be used.

Alternatively, the inference section 14 may adopt a method which, without using a template waveform, compares similarity levels among the four waveforms, and allows a waveform whose similarity levels with the other three waveforms produce the lowest average value to be used as the inference result. In this case, among the results of option inference, if the average value of the similarity levels associated with the first rank and that of the second rank are distant by a predetermined value or more, it can be said that there is a high certainty level.

In the case where the certainty level thus calculated is high, it is considered highly likely that the output of the inference section 14 is correct. In the case of a high certainty level, therefore, the number of confirmation flickers may be decreased from its initial setting value (e.g., 10 times) in order to reduce the overall selection time. In the case of a low certainty level, on the other hand, it is considered that the output of the inference section 14 may possibly be incorrect. Therefore, the number of confirmation flickers may be increased from its initial setting value in order to ensure a reliable confirmation.

Instead of a certainty level, it is also possible to utilize a proportion of results of determination by the determination section 16 as to whether the inferred option is incorrect or not. If the proportion with which the inferred option is determined as incorrect by the determination section 16 is equal to or greater than a prestored value, the selection flicker control section 12 may increase the number of flickers for the option. On the other hand, if the proportion is smaller than the prestored value, the selection flicker control section 12 may decrease the number of flickers for the option.

Another method for determining the number of flickers is a method which utilizes a certainty level of inference at the time of confirmation. From the event-related potential with respect to confirmation flickering, the determination section 16 is able to calculate a certainty level concerning whether a request of a retrial has been made. The certainty level may be either of the two states of "high" and "low" as mentioned above, or in the form of a numerical value. If the numerical value is equal to or greater than a predetermined threshold value, the certainty level may be categorized as "high", and if the numerical value is smaller than the threshold value, the certainty level may be categorized as "low". For example, the determination section 16 may determine that the certainty level is high when there is a high similarity level between the waveform of the event-related potential for the confirmation flickering and a prestored template waveform for use when a request of a retrial is made, or determine that the certainty level is low when there is a low similarity level between them.

If the certainty level is high, the number of confirmation flickers may be decreased from its initial setting value (e.g., 10 times). As a result, the amount of time until the option becomes finalized can be reduced. If the certainty level is low, the number of confirmation flickers may be increased from the initial setting value. As a result, even if an incorrect inference is made, a reliable confirmation is ensured.

The number of flickers for option inference and the number of flickers for confirmation flickering described above can be independently adjusted. Either one of them may be adjusted, or both of them may be adjusted. The timing of adjustment may be in real time, or, in view of a history of event-related potentials which have so far been acquired, the next option inference operation and/or confirmation flicker operation for the user may reflect the adjustment.

FIG. 12 is a flowchart showing a procedure of processing by the electroencephalogram interface system 1 of the present embodiment. The difference of the flowchart of FIG. 12 from the flowchart (FIG. 3(b)) of Embodiment 1 is that, next to step S92 of outputting a result, step S93 of adjusting the numbers of flickers is introduced.

By taking into consideration the event-related potentials which have been acquired up to that point in time, the selection flicker control section 12 and/or the confirmation flicker control section 15 calculate a certainty level(s) at the time of option inference and/or confirmation flickering, according to one of the methods mentioned above. Then, the selection flicker control section 12 and/or the confirmation flicker control section 15 adjust the number of confirmation flickers according to the certainty level. This allows an optimum number of selection flickers to be set for each user.

In this manner, through the operations of the electroencephalogram IF section 2 and the result confirmation section 3, the selection flicker control section 12 and the confirmation flicker control section 15 are able to adjust numbers of flickers. As a result, a suitable balance between the number of flickers and the distinction accuracy for each individual user can be established, thus allowing for an efficient use of the interface.

Embodiment 3

The above embodiments illustrate processes up to the determination of a need for correction through confirmation flickering. The present embodiment illustrates a method by which the electroencephalogram interface system automatically corrects an option when there is a need to correct an inferred option.

Note that the construction of the electroencephalogram interface system of the present embodiment is also the same as in Embodiment 1. Therefore, only those component elements which have different functions from Embodiment 1 will be described, while omitting the descriptions of any component elements having the same functions as in Embodiment 1.

Firstly, the reason why an automatic correction is possible will be described.

The inventors have analyzed data from a total of 96 trials, where 12 test subjects each made 8 trials of selections. FIG. 13A shows analysis results of the experimental data using the electroencephalogram interface system 1. This diagram shows results of making a trial-by-trial analysis as to where among all options is the amplitude level of an event-related potential (P300) corresponding to the correct option, and taking counts thereof. This indicates, in each case of inferring an option at step S40 of FIG. 3(b), the ordinal rank (i.e., how large) of the P300 amplitude for the correct option among all of the four event-related potentials (i.e., including the other options).

According to FIG. 13A, for example, it can be seen that the correct option registered the largest amplitude in 69 trials among the total of 96 trials. In the option inference at step S40 of FIG. 3(b), among the four event-related potentials based on the flickering of each option as a starting point, the option that is associated with an event-related potential whose amplitude near P300 ranks the largest is determined as the inferred option. In actuality, however, the electroencephalogram waveform does not always take the largest amplitude among the four options, due to fluctuations and mixing of noise. FIG. 13A shows this fact.

Among the total of 96 trials, there were 69 trials which arrived at the correct option and in which the P300 amplitude registered the largest for that option, accounting for 72% of the total. Therefore, if the confirmation flickering that is described in the present specification were not to be performed, the correctness rate of the inferred option would be 72%.

As the analysis results of the waveform amplitudes shown in the table of FIG. 13A indicate, regarding the P300 amplitude for the option which the user 10 wanted to select, there were 14 instances where it ranked second among the P300 amplitudes for the four options, 7 instances where it ranked third, and 6 instances where it ranked fourth. It can be seen from these results that, even if the presented option corresponding to the maximum amplitude happens to be incorrect (27 times out of 96 times in the table), there is a probability of ½ or more that the option with the second largest amplitude is correct (14 times out of 27 times).

Therefore, if it is determined in the confirmation inference at step S80 of FIG. 3(b) that the result inferred at step S40 is incorrect, a correction is made so as to reselect an option which ranks the second largest among the P300 amplitudes of event-related potentials associated with the highlighting of options when using the electroencephalogram interface. Evidently, the correct option is arrived at in more than half of the cases in this manner. This finding makes possible an automatic correction in the case where an inferred option is incorrect.

FIG. 13B shows results of studying effects of correction on the basis of the experimental data of FIG. 13A in terms of proportion. The proportion of the instances in which the inferred option is correct is 72%. In instances where the inferred option is incorrect (i.e., among the remaining 28%), if a correction is made to reselect the option that has evoked the second largest P300 amplitude, then the proportion of the instances in which the corrected option turns out correct will be 15%. Therefore, by tolerating a one-time correction of the option, the correct option will be reached 83 times (69 times+14 times) out of 96 times, meaning that the overall correctness rate is improved to 87% at the most.

The reason why many instances concentrate at the topmost two ranks of P300 amplitude may be that noise often occurs in abrupt manners, rather than exerting an averaged influence over all options. For example, a change in the electro-oculographic potential caused by a blink will affect the electroencephalogram in the form of an abrupt change. In this case, both the event-related potential corresponding to the correct option and the event-related potentials affected by the electro-oculographic potential will be diversely present among the event-related potential for the four options, which may account for the confusion between the first rank and the second rank.

Thus, a feasibility has been indicated that, based on the characteristic electroencephalogram component of the user 10 when an incorrect inference is made, it is possible to know at the apparatus side that the result of inference by the apparatus was incorrect, and that an automatic correction can also be made.

Next, a procedure of processing according to the present embodiment, which is based on the experimental results obtained above, will be described. FIG. 14 is a flowchart showing a procedure of incorrect inference detection and option correction. The detailed processes after the determination of the inferred option at step S40 and after in FIG. 3(b) are shown. The description of any process before step S30 in FIG. 3(b) is omitted.

At step S40, the output section 17 displays an inferred option.

At step S50, the confirmation flicker control section 15 performs confirmation flickering for allowing the inference result to be confirmed.

At step S80, the biological signal detection section 13 acquires an electroencephalogram (event-related potential) based on the confirmation flickering as a starting point. Then, the determination section 16 determines whether a component which asks for correction, e.g., P300, is contained in the event-related potential or not, and accordingly determines whether the inferred option is correct or not.

At step S81, the determination section 16 determines whether the component related to confirmation has been detected or not. If the P300 component is contained, the determination section 16 determines that correction is necessary, i.e., the inference result is incorrect, and proceeds to step S94. If the P300 component is not contained, control proceeds to step S97.

At step S97, the determination section 16 determines that there is no need for option correction, and, with the option inferred at step S40 as the final result, the process proceeds to the operation output of step S96.

At step S94, for correction of the inferred option, the inference section 14 extracts from the memory the event-related potential for the highlighting of each option as stored at step S30 of FIG. 3. Depending on the number of repetitions of step S30, each event-related potential may or may not have been subjected to an arithmetic mean process.

At step S95, from among the waveforms for the highlighting of the respective options extracted at step S61, the determination section 16 chooses the option whose amplitude is in the second rank as the end-result of correction. This illustrates a way of utilizing the finding that, when the first rank is incorrect, the option of the second rank will be correct with a probability of ½ or more.

At step S96, since the final option to be executed by the device has been determined, the output section 17 executes a process corresponding to that determined option. As a result, a device operation as desired by the user 10 is realized. For example, in a program-selecting operation on a television set as in the present embodiment, the channel is switched to the selected program, and the program of interest is displayed.

According to the above process, even if the electroencephalogram interface system 1 makes an incorrect option inference due to fluctuations in the electroencephalogram or mixing of noise, a different option from that option is newly chosen. From the perspective of the user 10, an incorrect option becomes automatically corrected in the electroencephalogram interface system 1, thereby reducing the number of re-manipulations. As a result, the manipulability of the electroencephalogram interface is improved.

One stipulation for automatic correction to work effectively is to remove noise. Various sources of noise are conceivable: device noises from outside the human body; electric-myographic or electro-oculographic potential noises from within the human body; background electroencephalogram not related to any interface manipulations; and so on. By minimizing these, even if an option inference fails, there will be an improved possibility that the correct option exists in the second rank.

Thus, when a correction needs to be made after confirmation flickering, an automatic correction can be performed, thus eliminating the need for any intent indication such as making another selection. As a result, the manipulability of the interface is enhanced.

Although Embodiments 1 to 3 above illustrate examples where an option is inferred and a confirmation determination for the inference result is performed by using P300 as an event-related potential. However, N200 may be used as the event-related potential. "N200" refers to, in an electroencephalogram signal from 100 milliseconds to 300 milliseconds based on the flickering of an option as a starting point, an event-related potential having a negative (minus-direction) peak in its amplitude. Note that "having a negative peak in amplitude" only requires having a local minimum, which is inclusive of a minimum value. This event-related potential N200 can be used in the inference section or the determination section. Any other electroencephalogram component can also be used so long as it is effective for the determination.

With respect to any one of Embodiments 1 to 3 described above, any process that was described by employing a flowchart can be implemented as a method of operating an electroencephalogram interface system, or as a program to be executed by a computer. Such a computer program may be distributed on the market in the form of a product recorded on a storage medium, such as a CD-ROM, or transmitted via telecommunication lines such as the Internet. When the computer program is executed by a computer, the processes described in the flowchart are carried out by the computer. The electroencephalogram IF section 2 and the result confirmation section 3 are implemented as a general-purpose processor (semiconductor circuit) executing a computer program. Alternatively, they may be implemented as a special processor in which such a computer program and a processor are integrated.

For example, FIG. 15 shows a hardware construction of the electroencephalogram IF providing apparatus 4. The electroencephalogram IF providing apparatus 4 includes a CPU 30, a memory 31, a graphic controller 32, and a communications controller 33. These are interconnected via a bus 34, such that mutual exchanges of data are possible.

The CPU 30 executes a computer program 35 which is stored in the memory 31. In accordance with the computer program 35, the electroencephalogram IF providing apparatus 4 realizes the above-described operations of the selection flicker control section 12, the inference section 14, the confirmation flicker control section 15, and the determination section 16.

In accordance with commands from the CPU 30, the graphic controller 32 causes the stimulation presentation section 11 to present a plurality of options, and perform selection flickering and confirmation flickering of the options. Moreover, in accordance with commands from the CPU 30, the communications controller 33 receives an electroencephalogram signal of a user which is measured by the biological signal detection section 13, and causes the output section 17 to execute a process which is in accordance with the result of determination by the determination section 16.

Note that the electroencephalogram IF providing apparatus 4 may be implemented as a single processor or circuit. Alternatively, each of the selection flicker control section 12, the inference section 14, the confirmation flicker control section 15, and the determination section 16 included in the electroencephalogram IF providing apparatus 4 may be provided as a processor or circuit, or any two or more of them may be provided as a single processor or circuit.

The electroencephalogram interface according to the present invention copes with the generic problems of an electroencephalogram, and is broadly applicable in scenes where an electroencephalogram interface is used for device control or the like.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An electroencephalogram interface system comprising:
  a presentation section for presenting a plurality of options to a user, the plurality of options being manipulable items concerning manipulations of a device;
  a selection flicker control section for flickering each of the plurality of options;
  a biological signal detection section for measuring an electroencephalogram signal from the user;
  an inference section for inferring one option corresponding to a desired manipulation of the user by utilizing an event-related potential of an electroencephalogram contained in the electroencephalogram signal, the event-related potential being based on the flickering of each of the plurality of options as a starting point;
  a confirmation flicker control section for effecting confirmation flickering of the one option inferred;
  a determination section for determining whether the inferred option corresponds to the desired manipulation of the user by utilizing an event-related potential of an electroencephalogram contained in the electroencephalogram signal, the event-related potential being based on the confirmation flickering of the one option as a starting point; and
  an output section for executing a process which is in accordance with a result of determination by the determination section.

2. The electroencephalogram interface system of claim 1, wherein at least one of the inference section and the confirmation flicker control section adjusts the number of times of flickering each of the plurality of options and/or the number of confirmation flickers, by using event-related potentials having been acquired up to a given point in time.

3. The electroencephalogram interface system of claim 2, wherein,
  at least the confirmation flicker control section adjusts the number of confirmation flickers; and
  by using the event-related potentials having been acquired up to the given point in time, the confirmation flicker control section calculates a certainty level, the certainty level being an index indicating how certain the option inferred by the inference section is to the user, and decreases the number of confirmation flickers if the certainty level is high, or increases the number of confirmation flickers if the certainty level is low.

4. The electroencephalogram interface system of claim 3, wherein the determination section calculates a certainty level concerning presence or absence of a request for changing the inferred option by using a similarity level, the similarity level being calculated based on a waveform of an event-related potential for the confirmation flickering and a prestored template waveform for use when a request of a retrial is made.

5. The electroencephalogram interface system of claim 2, wherein,
  at least the confirmation flicker control section adjusts the number of confirmation flickers;
  the determination section calculates a certainty level concerning presence or absence of a request for changing the inferred option by using an event-related potential concerning the confirmation flickering;
  when the certainty level is equal to or greater than a predetermined threshold value, the determination section categorizes the certainty level to be high, and the confirmation flicker control section decreases the number of confirmation flickers; and
  when the certainty level is smaller than the predetermined threshold value, the determination section categorizes the certainty level to be low, and the confirmation flicker control section increases the number of confirmation flickers.

6. The electroencephalogram interface system of claim 2, wherein the determination section calculates a certainty level concerning presence or absence of a request for changing the inferred option by using a similarity level, the similarity level being calculated based on a waveform of an event-related potential for the confirmation flickering and a prestored template waveform for use when a request of a retrial is made.

7. The electroencephalogram interface system of claim 6, wherein,
when a result of inference by the inference section is determined by the determination section as incorrect,
the selection flicker control section increases the number of flickers for each option if a proportion with which the result or results of inference are determined as incorrect is equal to or greater than a predetermined value, and the selection flicker control section decreases the number of flickers for each option if the proportion with which the result or results of inference are determined as incorrect is smaller than the predetermined value.

8. The electroencephalogram interface system of claim 1, wherein, by utilizing a proportion with which a result or results of inference by the inference section are determined by the determination section as incorrect, the selection flicker control section adjusts the number of flickers for each option.

9. The electroencephalogram interface system of claim 1, wherein the number of confirmation flickers controlled by the confirmation flicker control section is larger than the number of selection flickers controlled by the selection flicker control section.

10. The electroencephalogram interface system of claim 1, wherein,
the inference section infers an option for which a predetermined component of the event-related potential takes a largest amplitude to be the option corresponding to the desired manipulation of the user; and
when the inferred option is determined by the determination section as incorrect, the inference section re-infers an option for which the predetermined component takes a second largest amplitude to be the option corresponding to the desired manipulation of the user.

11. The electroencephalogram interface system of claim 1, wherein the inference section infers the option corresponding to the desired manipulation of the user by using a positive local maximum of an event-related potential from 200 milliseconds to 400 milliseconds based on the flickering of each option as a starting point, or a negative local minimum of an event-related potential from 100 milliseconds to 300 milliseconds based on the flickering of each option as a starting point.

12. The electroencephalogram interface system of claim 1, wherein, in determining whether the inferred option corresponds to the desired manipulation of the user, the determination section uses P300 or N200, where P300 is a positive local maximum of an event-related potential from 200 milliseconds to 400 milliseconds based on the confirmation flickering of the inferred option as a starting point, and N200 is a negative local minimum of an event-related potential from 100 milliseconds to 300 milliseconds based on the confirmation flickering of the inferred option as a starting point.

13. The electroencephalogram interface system of claim 1, wherein the inference section infers an option that corresponds to, among event-related potentials based on the flickering of the plurality of options as starting points, an event-related potential having a predetermined characteristic component to be the one option corresponding to the desired manipulation of the user.

14. The electroencephalogram interface system of claim 1, wherein,
when an event-related potential based on the flickering of the one option as a starting point contains a predetermined characteristic component, the determination section determines that the one option corresponds to the desired manipulation of the user; and
when an event-related potential based on the flickering of the one option as a starting point does not contain the predetermined characteristic component, the determination section determines that the one option does not correspond to the desired manipulation of the user.

15. An electroencephalogram interface providing apparatus comprising:
a selection flicker control section for flickering each of a plurality of options on a presentation section, the plurality of options being manipulable items concerning manipulations of a device;
an inference section for inferring one option corresponding to a desired manipulation of the user by utilizing an event-related potential of an electroencephalogram contained in an electroencephalogram signal from the user measured by a biological signal detection section, the event-related potential being based on the flickering of each of the plurality of options as a starting point;
a confirmation flicker control section for effecting confirmation flickering of the one option inferred; and
a determination section for determining whether the inferred option corresponds to the desired manipulation of the user by utilizing an event-related potential of an electroencephalogram contained in the electroencephalogram signal, the event-related potential being based on the confirmation flickering of the one option as a starting point, wherein
the electroencephalogram interface providing apparatus causes an output section to execute a process which is in accordance with a result of determination by the determination section.

16. A method of operating an electroencephalogram interface system, comprising the steps of:
presenting a plurality of options to a user, the plurality of options being manipulable items concerning manipulations of a device;
flickering each of the plurality of options;
measuring an electroencephalogram signal from the user;
inferring one option corresponding to a desired manipulation of the user by utilizing an event-related potential of an electroencephalogram contained in the electroencephalogram signal, the event-related potential being based on the flickering of each of the plurality of options as a starting point;
effecting confirmation flickering of the one option inferred;
determining whether the inferred option is an option corresponding to the desired manipulation of the user by utilizing an event-related potential of an electroencephalogram contained in the electroencephalogram signal, the event-related potential being based on the confirmation flickering of the one option as a starting point; and
executing a process which is in accordance with a result of determination by the determination step.

17. A computer program, stored on a non-transitory computer-readable medium, to be executed by a computer mounted in an electroencephalogram interface providing apparatus, wherein
the computer program causes the computer to execute the steps of:
causing a presentation section to present a plurality of options, the plurality of options being manipulable items concerning manipulations of a device;
flickering each of the plurality of options;

receiving an electroencephalogram signal from the user measured by a biological signal detection section;

inferring one option corresponding to a desired manipulation of the user by utilizing an event-related potential of an electroencephalogram contained in the electroencephalogram signal, the event-related potential being based on the flickering of each of the plurality of options as a starting point;

effecting confirmation flickering of the one option inferred;

determining whether the inferred option is an option corresponding to the desired manipulation of the user by utilizing an event-related potential of an electroencephalogram contained in the electroencephalogram signal, the event-related potential being based on the confirmation flickering of the one option as a starting point; and causing an output section to execute a process which is in accordance with a result of determination by the determination step.

* * * * *